(12) United States Patent
Coleman et al.

(10) Patent No.: US 8,242,121 B2
(45) Date of Patent: Aug. 14, 2012

(54) PYRIDYL PIPERIDINE OREXIN RECEPTOR ANTAGONISTS

(75) Inventors: Paul J. Coleman, Harleysville, PA (US); John D. Schreier, Red Hill, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 339 days.

(21) Appl. No.: 12/600,388

(22) PCT Filed: May 22, 2008

(86) PCT No.: PCT/US2008/006563
§ 371 (c)(1), (2), (4) Date: Nov. 16, 2009

(87) PCT Pub. No.: WO2008/147518
PCT Pub. Date: Dec. 4, 2008

(65) Prior Publication Data
US 2010/0168134 A1 Jul. 1, 2010

Related U.S. Application Data

(60) Provisional application No. 60/931,458, filed on May 23, 2007.

(51) Int. Cl.
C07D 401/14 (2006.01)
A61K 31/4525 (2006.01)

(52) U.S. Cl. ........................................ 514/256; 544/333

(58) Field of Classification Search .................. 544/333, 544/405; 546/194; 514/256, 318
See application file for complete search history.

(56) References Cited

U.S. PATENT DOCUMENTS

| | | | |
|---|---|---|---|
| 4,643,995 A | 2/1987 | Engel et al. |
| 6,677,354 B2 | 1/2004 | Branch et al. |
| 6,784,192 B2 | 8/2004 | Ozaki et al. |
| 6,943,160 B2 | 9/2005 | Branch et al. |
| 6,951,882 B2 | 10/2005 | Carruthers et al. |
| 7,166,608 B2 | 1/2007 | Branch et al. |
| 7,235,545 B2 | 6/2007 | Burgey et al. |
| 7,365,077 B2 | 4/2008 | Branch et al. |
| 7,423,052 B2 | 9/2008 | Chan et al. |
| 7,763,638 B2 | 7/2010 | Aissaoui et al. |
| 7,943,645 B2 | 5/2011 | Chan et al. |
| 7,951,797 B2 | 5/2011 | Breslin et al. |
| 2004/0143115 A1 | 7/2004 | Branch et al. |
| 2004/0180887 A1 | 9/2004 | Branch et al. |
| 2004/0192673 A1 | 9/2004 | Gailliard et al. |
| 2004/0215014 A1 | 10/2004 | Chan et al. |
| 2006/0142263 A1 | 6/2006 | Geralch et al. |
| 2006/0166966 A1 | 7/2006 | Black |
| 2007/0043037 A1 | 2/2007 | Aranyi et al. |
| 2008/0132490 A1 | 6/2008 | Bergman et al. |
| 2009/0215742 A1 | 8/2009 | Funk et al. |
| 2010/0069418 A1 | 3/2010 | Aissaoui et al. |
| 2010/0168134 A1 | 7/2010 | Breslin et al. |
| 2011/0165632 A1 | 7/2011 | Campeau et al. |
| 2011/0201632 A1 | 8/2011 | Breslin et al. |
| 2011/0201652 A1 | 8/2011 | Cox et al. |
| 2011/0207715 A1 | 8/2011 | Cox et al. |
| 2011/0251237 A1 | 10/2011 | Breslin et al. |
| 2011/0257198 A1 | 10/2011 | Alvaro et al. |
| 2011/0263643 A1 | 10/2011 | Cox et al. |
| 2011/0312961 A1 | 12/2011 | Cox et al. |

FOREIGN PATENT DOCUMENTS

| | | |
|---|---|---|
| EP | 2152690 B1 | 1/2012 |
| WO | WO9909024 | 2/1999 |
| WO | WO9958533 | 11/1999 |
| WO | WO0047576 | 8/2000 |
| WO | WO0047577 | 8/2000 |
| WO | WO0047580 | 8/2000 |
| WO | WO0185693 | 4/2001 |
| WO | WO0168609 | 9/2001 |
| WO | WO0196302 | 12/2001 |
| WO | WO0251232 | 4/2002 |
| WO | WO0244172 | 6/2002 |
| WO | WO02051838 | 7/2002 |
| WO | WO02089800 | 11/2002 |

(Continued)

OTHER PUBLICATIONS

Rodgers et al., Orexins and appetite regulation, Neuroleptides (2002) 36(5): 303-325.*

(Continued)

*Primary Examiner* — Deepak Rao
(74) *Attorney, Agent, or Firm* — J. Eric Thies; Gerard M. Devlin

(57) ABSTRACT

The present invention is directed to pyridyl piperidine compounds of formula (I) which are antagonists of orexin receptors, and which are useful' in the treatment or prevention of neurological and psychiatric disorders and diseases in which orexin receptors are involved. The invention is also directed to pharmaceutical compositions comprising these compounds and the use of these compounds and compositions in the prevention or treatment of such diseases in which orexin receptors are involved.

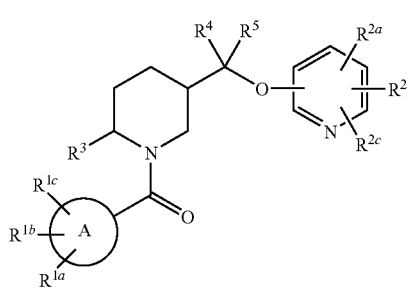

9 Claims, No Drawings

FOREIGN PATENT DOCUMENTS

| | | |
|---|---|---|
| WO | WO02090355 | 11/2002 |
| WO | WO03002559 | 1/2003 |
| WO | WO03002561 | 1/2003 |
| WO | WO03032991 | 4/2003 |
| WO | WO03037847 | 5/2003 |
| WO | WO03041711 | 5/2003 |
| WO | WO03051368 | 6/2003 |
| WO | WO03051871 | 6/2003 |
| WO | WO03051872 | 6/2003 |
| WO | WO03051873 | 6/2003 |
| WO | WO2004004733 | 1/2004 |
| WO | WO2004026866 | 4/2004 |
| WO | WO2004033418 | 4/2004 |
| WO | WO2004041791 | 5/2004 |
| WO | WO2004041807 | 5/2004 |
| WO | WO2004041816 | 5/2004 |
| WO | WO2004052876 | 6/2004 |
| WO | WO2004083218 | 9/2004 |
| WO | WO2004085403 | 10/2004 |
| WO | WO2004096780 | 11/2004 |
| WO | WO2005060959 | 7/2005 |
| WO | WO2005075458 | 8/2005 |
| WO | WO2005118548 | 12/2005 |
| WO | WO2006110626 | 4/2006 |
| WO | WO2006067224 | 6/2006 |
| WO | WO 2006/117669 * | 11/2006 |
| WO | WO2006117669 | 11/2006 |
| WO | WO2006127550 | 11/2006 |
| WO | WO2007025069 | 3/2007 |
| WO | WO2007061763 | 5/2007 |
| WO | WO2007116374 | 10/2007 |
| WO | WO2007019234 | 11/2007 |
| WO | WO2007122591 | 11/2007 |
| WO | WO2007126934 | 11/2007 |
| WO | WO2007126935 | 11/2007 |
| WO | WO2008008517 | 1/2008 |
| WO | WO2008008518 | 1/2008 |
| WO | WO2008008551 | 1/2008 |
| WO | WO2008020405 | 2/2008 |
| WO | WO2008026149 | 3/2008 |
| WO | WO2008038251 | 4/2008 |
| WO | WO2008065626 | 6/2008 |
| WO | WO2008147518 | 12/2008 |
| WO | WO2009124956 | 10/2009 |
| WO | WO2009143033 | 11/2009 |
| WO | WO2010048010 | 4/2010 |
| WO | WO2010048012 | 4/2010 |
| WO | WO2010048013 | 4/2010 |
| WO | WO2010048014 | 4/2010 |
| WO | WO2010048016 | 4/2010 |
| WO | WO2010048017 | 4/2010 |
| WO | WO2011023578 | 3/2011 |

OTHER PUBLICATIONS

Roecker et al., PubMed Abstract (Curr Top Med Chem), 2008.*
Willie et al., PubMed Abstract (Annu Rev Neurosci), 2001.*
J. Cai et al., "Antagonists of the Orexin Receptors", Expert Opinion, 2006, vol. 16, pp. 631-636.
P. Coleman et al., "Orexin Receptor Antagonists: A Review of Promising Compounds Patented Since 2006", Expert Opinion, vol. 20, pp. 307-324.
M. Bingham et al., "Eating, Sleeping and Rewarding: Orexin Receptors and Their Antagonists", Current Opinion in Drug Discovery & Development, 2006, vol. 9, pp. 551-559.
A. Roecker et al., "Orexin Receptor Antagonists: Medicinal Chemistry and Therapeutic Potential", Current Topics in Medicinal Chemistry, 2008, vol. 8, pp. 977-987.
P. Coleman et al., "Discovery Dual Orexin Receptor Antagonists (DORAs) for the Treatment of Insomnia", Current Topics in Medicinal Chemistry, 2011, vol. 11, pp. 696-725.
P. Coleman et al., "Discovery of [(2R,5R)-5-{[(5-Fluoropropyridin-2-yl)Oxy]Methyl]}-2-Methylpiperidin-1-yl][5-Methyl-2-(Pyrimidin-2-yl) Phenyl] Methanone (MK-6096): A Dual Orexin Receptor Antagonist with Potent Sleep-Promoting Properties", ChemMedChem, 2012, vol. 7, pp. 415-424.
C. Winrow et al, "Pharmacological Characterization of MK-6096—A Dual Orexin Receptor Antagonist for Insomnia", Neuropharmacology, 2012, pp. 978-987.

* cited by examiner

PYRIDYL PIPERIDINE OREXIN RECEPTOR ANTAGONISTS

CROSS REFERENCE TO RELATED APPLICATIONS

This application is a U.S. National Phase application under 35 U.S.C. §371 of PCT Application No. PCT/US2008/006563, filed May 22, 2008, which claims priority under 35 U.S.C. §119 from US Application No. 60/931,458, filed May 23, 2007.

BACKGROUND OF THE INVENTION

The orexins (hypocretins) comprise two neuropeptides produced in the hypothalamus: the orexin A (OX-A) (a 33 amino acid peptide) and the orexin B (OX-B) (a 28 amino acid peptide) (Sakurai T. et al., Cell, 1998, 92, 573-585). Orexins are found to stimulate food consumption in rats suggesting a physiological role for these peptides as mediators in the central feedback mechanism that regulates feeding behaviour (Sakurai T. et al., Cell, 1998, 92, 573-585). Orexins regulate states of sleep and wakefulness opening potentially novel therapeutic approaches for narcoleptic or insomniac patients (Chemelli R. M. et al., Cell, 1999, 98, 437-451). Orexins have also been indicated as playing a role in arousal, reward, learning and memory (Harris, et al., Trends Neurosci., 2006, 29 (10), 571-577). Two orexin receptors have been cloned and characterized in mammals. They belong to the super family of G-protein coupled receptors (Sakurai T. et al., Cell, 1998, 92, 573-585): the orexin-1 receptor (OX or OX1R) is selective for OX-A and the orexin-2 receptor (OX2 or OX2R) is capable to bind OX-A as well as OX-B. The physiological actions in which orexins are presumed to participate are thought to be expressed via one or both of OX 1 receptor and OX 2 receptor as the two subtypes of orexin receptors.

Orexin receptors are found in the mammalian brain and may have numerous implications in pathologies such as depression; anxiety; addictions; obsessive compulsive disorder; affective neurosis; depressive neurosis; anxiety neurosis; dysthymic disorder; behaviour disorder; mood disorder; sexual dysfunction; psychosexual dysfunction; sex disorder; schizophrenia; manic depression; delirium; dementia; severe mental retardation and dyskinesias such as Huntington's disease and Tourette syndrome; eating disorders such as anorexia, bulimia, cachexia, and obesity; addictive feeding behaviors; binge/purge feeding behaviors; cardiovascular diseases; diabetes; appetite/taste disorders; emesis, vomiting, nausea; asthma; cancer; Parkinson's disease; Cushing's syndrome/disease; basophile adenoma; prolactinoma; hyperprolactinemia; hypophysis tumour/adenoma; hypothalamic diseases; inflammatory bowel disease; gastric diskinesia; gastric ulcers; Froehlich's syndrome; adrenohypophysis disease; hypophysis disease; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; disturbed biological and circadian rhythms; sleep disturbances associated with diseases such as neurological disorders, neuropathic pain and restless leg syndrome; heart and lung diseases, acute and congestive heart failure; hypotension; hypertension; urinary retention; osteoporosis; angina pectoris; myocardinal infarction; ischemic or haemorrhagic stroke; subarachnoid hemorrhage; ulcers; allergies; benign prostatic hypertrophy; chronic renal failure; renal disease; impaired glucose tolerance; migraine; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; conditions associated with visceral pain such as irritable bowel syndrome, and angina; migraine; urinary bladder incontinence e.g. urge incontinence; tolerance to narcotics or withdrawal from narcotics; sleep disorders; sleep apnea; narcolepsy; insomnia; parasomnia; jet lag syndrome; and neurodegenerative disorders including nosological entities such as disinhibition-dementia-parkinsonism-amyotrophy complex; pallido-ponto-nigral degeneration; epilepsy; seizure disorders and other diseases related to general orexin system dysfunction.

Certain orexin receptor antagonists are disclosed in PCT patent publications WO 99/09024, WO 99/58533, WO 00/47576, WO 00/47577, WO 00/47580, WO 01/68609, WO 01/85693, WO 01/96302, WO 2002/044172, WO 2002/051232, WO 2002/051838, WO 2002/089800, WO 2002/090355, WO 2003/002559, WO 2003/002561, WO 2003/032991, WO 2003/037847, WO 2003/041711, WO 2003/051368, WO 2003/051872, WO 2003/051873, WO 2004/004733, WO 2004/026866, WO 2004/033418, WO 2004/041807, WO 2004/041816, WO 2004/052876, WO 2004/083218, WO 2004/085403, WO 2004/096780, WO 2005/060959, WO 2005/075458, WO2005/118548, WO 2006/067224, WO 2006/110626, WO 2006/127550, WO 2007/019234, WO 2007/025069, WO 2007/061763, WO 2007/116374, WO 2007/122591, WO 2007/126934, WO 2007/126935, WO 2008/008517, WO 2008/008518, WO 2008/008551, WO 2008/020405, WO 2008//026149, WO 2008/038251.

SUMMARY OF THE INVENTION

The present invention is directed to pyridyl piperidine compounds which are antagonists of orexin receptors, and which are useful in the treatment or prevention of neurological and psychiatric disorders and diseases in which orexin receptors are involved. The invention is also directed to pharmaceutical compositions comprising these compounds and the use of these compounds and compositions in the prevention or treatment of such diseases in which orexin receptors are involved.

DETAILED DESCRIPTION OF THE INVENTION

The present invention is directed to compounds of the formula I:

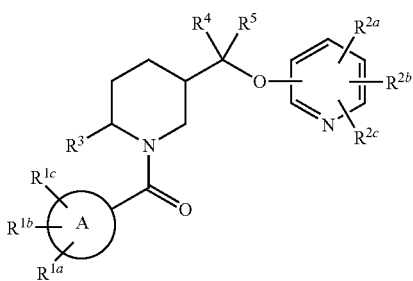

wherein:

A is selected from the group consisting of phenyl, napthyl and heteroaryl;

$R^{1a}$, $R^{1b}$ and $R^{1c}$ may be absent if the valency of $A^1$ does not permit such substitution and are independently selected from the group consisting of:
(1) hydrogen,
(2) halogen,
(3) hydroxyl,
(4) —(C=O)$_m$—O$_n$—C$_{1-6}$alkyl, where m is 0 or 1, n is 0 or 1 (wherein if m is 0 or n is 0, a bond is present) and where the alkyl is unsubstituted or substituted with one or more substituents selected from $R^{13}$,
(5) —(C=O)$_m$—O$_n$—C$_3$-C$_6$cycloalkyl, where the cycloalkyl is unsubstituted or substituted with one or more substituents selected from $R^{13}$,
(6) —(C=O)$_m$—C$_{2-4}$alkenyl, where the alkenyl is unsubstituted or substituted with one or more substituents selected from $R^{13}$,
(7) —(C=O)$_m$—C$_{2-4}$alkynyl, where the alkynyl is unsubstituted or substituted with one or more substituents selected from $R^{13}$,
(8) —(C=O)$_m$—O$_n$-phenyl or —(C=O)$_m$—O$_n$-napthyl, where the phenyl or napthyl is unsubstituted or substituted with one or more substituents selected from $R^{13}$,
(9) —(C=O)$_m$—O$_n$-heterocycle, where the heterocycle is unsubstituted or substituted with one or more substituents selected from $R^{13}$,
(10) —(C=O)$_m$—NR$^{10}$R$^{11}$, wherein $R^{10}$ and $R^{11}$ are independently selected from the group consisting of:
  (a) hydrogen,
  (b) C$_{1-6}$alkyl, which is unsubstituted or substituted with $R^{13}$,
  (c) C$_{3-6}$alkenyl, which is unsubstituted or substituted with $R^{13}$,
  (d) C$_{3-6}$alkynyl, which is unsubstituted or substituted with $R^{13}$,
  (e) C$_{3-6}$cycloalkyl which is unsubstituted or substituted with $R^{13}$,
  (f) phenyl, which is unsubstituted or substituted with $R^{13}$, and
  (g) heterocycle, which is unsubstituted or substituted with $R^{13}$,
(11) —S(O)$_2$—NR$^{10}$R$^{11}$,
(12) —S(O)$_q$—R$^{12}$, where q is 0, 1 or 2 and where $R^{12}$ is selected from the definitions of $R^{10}$ and $R^{11}$,
(13) —CO$_2$H,
(14) —CN, and
(15) —NO$_2$;

$R^{2a}$, $R^{2b}$ and $R^{2c}$ are independently selected from the group consisting of:
(1) hydrogen,
(2) halogen,
(3) hydroxyl,
(4) —(C=O)$_m$—O$_n$—C$_{1-6}$alkyl, where the alkyl is unsubstituted or substituted with one or more substituents selected from $R^{13}$,
(5) —(C=O)$_m$—O$_n$—C$_{3-6}$cycloalkyl, where the cycloalkyl is unsubstituted or substituted with one or more substituents selected from $R^{13}$,
(6) —(C=O)$_m$—C$_{2-4}$alkenyl, where the alkenyl is unsubstituted or substituted with one or more substituents selected from $R^{13}$,
(7) —(C=O)$_m$—C$_{2-4}$alkynyl, where the alkynyl is unsubstituted or substituted with one or more substituents selected from $R^{13}$,
(8) —(C=O)$_m$—O$_n$-phenyl or —(C=O)$_m$—O$_n$-napthyl, where the phenyl or napthyl is unsubstituted or substituted with one or more substituents selected from $R^{13}$,
(9) (C=O)$_m$—O$_n$-heterocycle, where the heterocycle is unsubstituted or substituted with one or more substituents selected from $R^{13}$,
(10) —(C=O)$_m$—NR$^{10}$R$^{11}$,
(11) —S(O)$_2$—NR$^{10}$R$^{11}$,
(12) —S(O)$_q$—R$^{12}$,
(13) —CO$_2$H,
(14) —CN, and
(15) —NO$_2$;

$R^3$ is hydrogen, C$_{1-6}$alkyl or C$_{3-6}$cycloalkyl, which is unsubstituted or substituted with one or more substituents selected from $R^{13}$;

$R^4$ and $R^5$ are independently selected from hydrogen and C$_{1-6}$alkyl, which is unsubstituted or substituted with one or more substituents selected from $R^{13}$, or $R^4$ and $R^5$ may be joined together to form a C$_{3-6}$cycloalkyl with the carbon atom to which they are attached, where the cycloalkyl is unsubstituted or substituted with one or more substituents selected from $R^{13}$;

$R^{13}$ is selected from the group consisting of:
(1) halogen,
(2) hydroxyl,
(3) —(C=O)$_m$—O$_n$—C$_{1-6}$alkyl, where the alkyl is unsubstituted or substituted with one or more substituents selected from $R^{14}$,
(4) —O$_n$—(C$_{1-3}$)perfluoroalkyl,
(5) —(C=O)$_m$—O$_n$—C$_{3-6}$cycloalkyl, where the cycloalkyl is unsubstituted or substituted with one or more substituents selected from $R^{14}$,
(6) —(C=O)$_m$—C$_{2-4}$alkenyl, where the alkenyl is unsubstituted or substituted with one or more substituents selected from $R^{14}$,
(7) —(C=O)$_m$—C$_{2-4}$alkynyl, where the alkynyl is unsubstituted or substituted with one or more substituents selected from $R^{14}$,
(8) —(C=O)$_m$—O$_n$-phenyl or —(C=O)$_m$—O$_n$-napthyl, where the phenyl or napthyl is unsubstituted or substituted with one or more substituents selected from $R^{14}$,
(9) —(C=O)$_m$—O$_n$-heterocycle, where the heterocycle is unsubstituted or substituted with one or more substituents selected from $R^{14}$,
(10) —(C=O)$_m$—NR$^{10}$R$^{11}$,
(11) —S(O)$_2$—NR$^{10}$R$^{11}$,
(12) —S(O)$_q$—R$^{12}$,
(13) —CO$_2$H,
(14) —CN, and
(15) —NO$_2$;

$R^{14}$ is selected from the group consisting of:
(1) hydroxyl,
(2) halogen,
(3) C$_{1-6}$alkyl, (4) —$C_{3-6}$cycloalkyl,
(5) —O—$C_{1-6}$alkyl,
(6) —O(C=O)—$C_{1-6}$alkyl,
(7) —NH—$C_{1-6}$alkyl,
(8) phenyl,
(9) heterocycle,
(10) —$CO_2H$, and
(11) —CN;

or a pharmaceutically acceptable salt thereof.

An embodiment of the present invention includes compounds of the formula Ia:

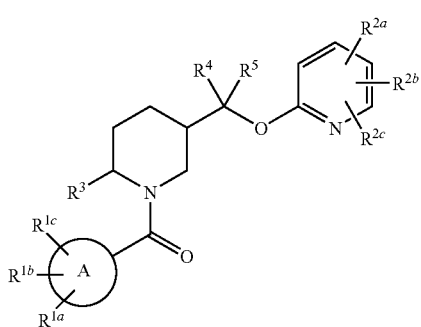

wherein A, $R^{1a}$, $R^{1b}$, $R^{1c}$, $R^{2a}$, $R^{2b}$, $R^{2c}$, $R^3$, $R^4$ and $R^5$ are defined herein; or a pharmaceutically acceptable salt thereof.

An embodiment of the present invention includes compounds of the formula Ia':

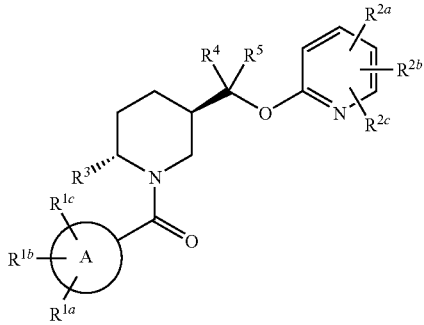

wherein A, $R^{1a}$, $R^{1b}$, $R^{1c}$, $R^{2a}$, $R^{2b}$, $R^{2c}$, $R^3$, $R^4$ and $R^5$ are defined herein; or a pharmaceutically acceptable salt thereof.

An embodiment of the present invention includes compounds of the formula Ia":

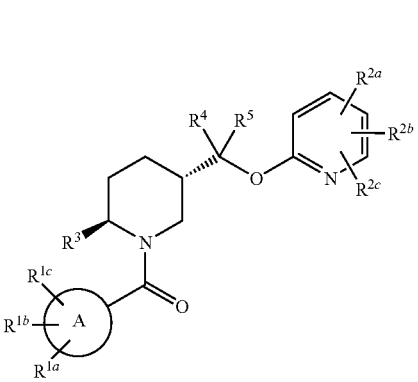

wherein A, $R^{1a}$, $R^{1b}$, $R^{1c}$, $R^{2a}$, $R^{2b}$, $R^{2c}$, $R^3$, $R^4$ and $R^5$ are defined herein; or a pharmaceutically acceptable salt thereof.

An embodiment of the present invention includes compounds of the formula Ib:

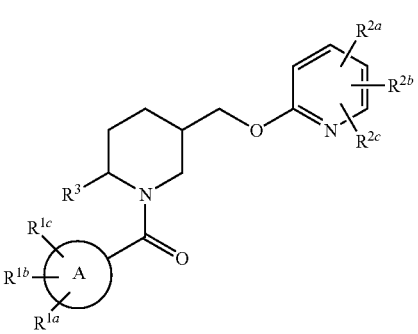

wherein A, $R^{1a}$, $R^{1b}$, $R^{1c}$, $R^{2a}$, $R^{2b}$, $R^{2c}$ and $R^3$ are defined herein; or a pharmaceutically acceptable salt thereof.

An embodiment of the present invention includes compounds of the formula Ic:

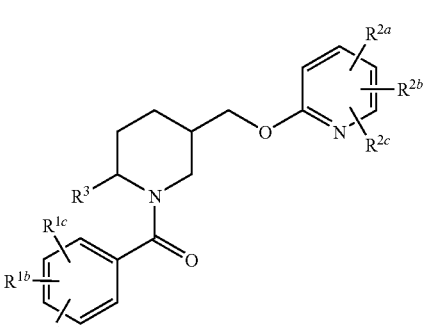

wherein A, $R^{1a}$, $R^{1b}$, $R^{1c}$, $R^{2a}$, $R^{2b}$, $R^{2c}$ and $R^3$ are defined herein; or a pharmaceutically acceptable salt thereof.

An embodiment of the present invention includes compounds of the formula Id:

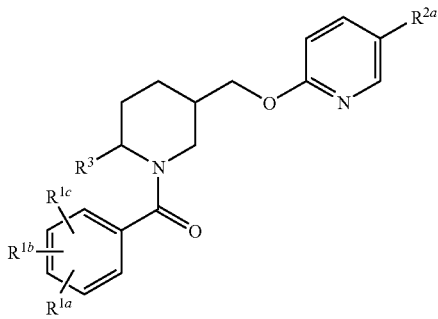

wherein $R^{1a}$, $R^{1b}$, $R^{1c}$, $R^{2a}$ and $R^3$ are defined herein; or a pharmaceutically acceptable salt thereof.

An embodiment of the present invention includes compounds of the formula Ie:

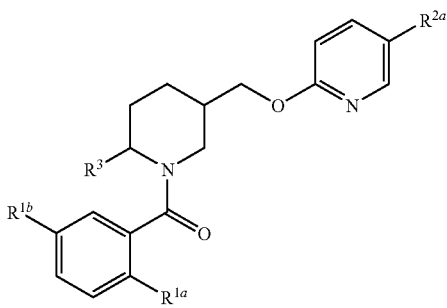

wherein $R^{1a}$, $R^{1b}$, $R^{2a}$ and $R^3$ are defined herein; or a pharmaceutically acceptable salt thereof.

An embodiment of the present invention includes compounds of the formula If:

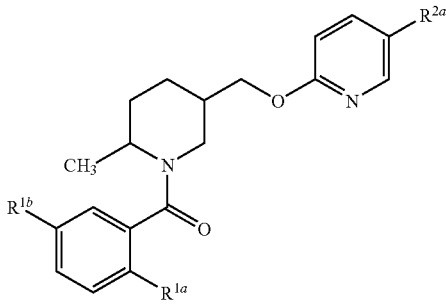

wherein $R^{1a}$, $R^{1b}$ and $R^{2a}$ are defined herein; or a pharmaceutically acceptable salt thereof.

An embodiment of the present invention includes compounds wherein $A^1$ is phenyl. An embodiment of the present invention includes compounds wherein $A^1$ is heteroaryl. An embodiment of the present invention includes compounds wherein $A^1$ is pyrazolyl. An embodiment of the present invention includes compounds wherein $A^1$ is thiazolyl.

An embodiment of the present invention includes compounds wherein $R^{1a}$, $R^{1b}$ and $R^{1c}$ are independently selected from the group consisting of:
(1) hydrogen,
(2) halogen,
(3) hydroxyl,
(4) $C_{1-6}$alkyl, which is unsubstituted or substituted with halogen, hydroxyl, phenyl or napthyl,
(5) —O—$C_{1-6}$alkyl, which is unsubstituted or substituted with halogen, hydroxyl or phenyl,
(6) heteroaryl, wherein heteroaryl is selected from triazolyl, oxazolyl, pyrrolyl, imidazolyl, indolyl, pyridyl, and pyrimidinyl, which is unsubstituted or substituted with halogen, hydroxyl, $C_{1-6}$alkyl, —O—$C_{1-6}$alkyl or —NO$_2$,
(7) phenyl, which is unsubstituted or substituted with halogen, hydroxyl, $C_{1-6}$alkyl, —O—$C_{1-6}$alkyl or —NO$_2$,
(8) —O-phenyl, which is unsubstituted or substituted with halogen, hydroxyl, $C_{1-6}$alkyl, —O—$C_{1-6}$alkyl or —NO$_2$, and
(9) —NH—$C_{1-6}$alkyl, or —N($C_{1-6}$alkyl)($C_{1-6}$alkyl), which is unsubstituted or substituted with halogen, hydroxyl, $C_{1-6}$alkyl, —O—$C_{1-6}$alkyl or —NO$_2$.

An embodiment of the present invention includes compounds wherein $R^{1a}$, $R^{1b}$ and $R_{1c}$ are independently selected from the group consisting of:
(1) hydrogen,
(2) halogen,
(3) hydroxyl,
(4) $C_{1-6}$alkyl, which is unsubstituted or substituted with halogen, hydroxyl or phenyl or napthyl,
(5) —O—$C_{1-6}$alkyl, which is unsubstituted or substituted with halogen, hydroxyl or phenyl,
(6) heteroaryl, wherein heteroaryl is selected from triazolyl, oxazolyl and pyrimidinyl, which is unsubstituted or substituted with halogen, hydroxyl or $C_{1-6}$alkyl, and
(7) phenyl, which is unsubstituted or substituted with halogen, hydroxyl or $C_{1-6}$alkyl.

An embodiment of the present invention includes compounds wherein $R^{1a}$, $R^{1b}$, and $R^{1c}$ are independently selected from the group consisting of:
(1) hydrogen,
(2) halogen,
(3) $C_{1-6}$alkyl,
(4) triazolyl,
(5) oxazolyl,
(6) pyrimidinyl, and
(7) phenyl.

An embodiment of the present invention includes compounds wherein $R^{1a}$, $R^{1b}$ and $R^{1c}$ are independently selected from the group consisting of:
(1) hydrogen,
(2) chloro,
(3) fluororo,
(4) methyl,
(5) triazolyl,
(6) oxazolyl,
(7) pyrimidinyl, and
(8) phenyl.

An embodiment of the present invention includes compounds wherein $R^{2a}$, $R^{2b}$ and $R^{2c}$ are independently selected from the group consisting of:
(1) hydrogen,
(2) halogen,
(3) hydroxyl,
(4) $C_{1-6}$alkyl, which is unsubstituted or substituted with halogen, hydroxyl or phenyl or napthyl,
(5) —O—$C_{1-6}$alkyl, which is unsubstituted or substituted with halogen, hydroxyl or phenyl,
(6) heteroaryl, wherein heteroaryl is selected from pyrrolyl, imidazolyl, indolyl, pyridyl, and pyrimidinyl, which is unsubstituted or substituted with halogen, hydroxyl, $C_{1-6}$alkyl, $C_{1-6}$alkyl or —$NO_2$,
(7) phenyl, which is unsubstituted or substituted with halogen, hydroxyl, $C_{1-6}$alkyl, —O—$C_{1-6}$alkyl or —$NO_2$,
(8) —O-phenyl, which is unsubstituted or substituted with halogen, hydroxyl, $C_{1-6}$alkyl, —O—$C_{1-6}$alkyl or —$NO_2$, and
(9) —NH—$C_{1-6}$alkyl, or —N($C_{1-6}$alkyl)($C_{1-6}$alkyl), which is unsubstituted or substituted with halogen, hydroxyl, $C_{1-6}$alkyl, —O—$C_{1-6}$alkyl or —$NO_2$.

An embodiment of the present invention includes compounds wherein $R^{2a}$, $R^{2b}$ and $R^{2c}$ are independently selected from the group consisting of:
(1) hydrogen,
(2) halogen,
(3) hydroxyl,
(4) $C_{1-6}$alkyl, which is unsubstituted or substituted with halogen, hydroxyl or phenyl,
(5) —O—$C_{1-6}$alkyl, which is unsubstituted or substituted with halogen, hydroxyl or phenyl, and
(6) —NH—$C_{1-6}$alkyl, or —N($C_{1-6}$alkyl)($C_{1-6}$alkyl), which is unsubstituted or substituted with halogen.

An embodiment of the present invention includes compounds wherein $R^{2a}$, $R^{2b}$ and $R^{2c}$ are independently selected from the group consisting of:
(1) hydrogen,
(2) halogen,
(3) $C_{1-6}$alkyl, which is unsubstituted or substituted with halogen,
(4) —O—$C_{1-6}$alkyl, which is unsubstituted or substituted with halogen, and
(5) —NH—$C_{1-6}$alkyl, or —N($C_{1-6}$alkyl)($C_{1-6}$alkyl), which is unsubstituted or substituted with halogen.

An embodiment of the present invention includes compounds wherein $R^{2a}$, $R^{2b}$ and $R^{2c}$ are independently selected from the group consisting of:
(1) hydrogen,
(2) chloro,
(3) fluoro,
(4) bromo,
(5) methoxy,
(6) t-butoxy,
(7) difluoromethyl, and
(8) trifluoromethyl.

An embodiment of the present invention includes compounds wherein $R^{2a}$, $R^{2b}$ and $R^{2c}$ are independently selected from the group consisting of:
(1) hydrogen,
(2) fluoro, and
(3) trifluoromethyl.

An embodiment of the present invention includes compounds wherein $R^3$ is hydrogen, $C_{1-6}$alkyl or $C_3$-$C_6$cycloalkyl. An embodiment of the present invention includes compounds wherein $R^3$ is other than hydrogen. An embodiment of the present invention includes compounds wherein $R^3$ is $C_{1-6}$alkyl. An embodiment of the present invention includes compounds wherein $R^3$ is $C_{3-6}$cycloalkyl. An embodiment of the present invention includes compounds wherein $R^3$ is methyl or ethyl. An embodiment of the present invention includes compounds wherein $R^3$ is methyl. An embodiment of the present invention includes compounds wherein $R^3$ is in the trans configuration on the piperidine ring relative to the pyridyloxymethyl substituent. An embodiment of the present invention includes compounds wherein $R^3$ is in the cis configuration on the piperidine ring relative to the pyridyloxymethyl substituent. An embodiment of the present invention includes compounds wherein $R^3$ is in the R configuration on the piperidine ring. An embodiment of the present invention includes compounds wherein the substituent at the 6-position of the piperidine ring is in the R configuration. An embodiment of the present invention includes compounds wherein pyridyloxymethyl group is in the R configuration on the piperidine ring. An embodiment of the present invention includes compounds wherein the substituent at the 3-position of the piperidine ring is in the R configuration.

An embodiment of the present invention includes compounds wherein $R^4$ is hydrogen or $C_{1-6}$alkyl. An embodiment of the present invention includes compounds wherein $R^4$ is hydrogen or methyl. An embodiment of the present invention includes compounds wherein $R^4$ is hydrogen. An embodiment of the present invention includes compounds wherein $R^5$ is hydrogen or $C_{1-6}$alkyl. An embodiment of the present invention includes compounds wherein $R^5$ is hydrogen or methyl. An embodiment of the present invention includes compounds wherein $R^5$ is hydrogen.

Specific embodiments of the present invention include a compound which is selected from the group consisting of the subject compounds of the Examples herein or a pharmaceutically acceptable salt thereof.

The compounds of the present invention may contain one or more asymmetric centers and can thus occur as "stereoisomers" including racemates and racemic mixtures, enantiomeric mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the scope of this invention. The present invention is meant to comprehend all such isomeric forms of these compounds. When bonds to the chiral carbon are depicted as straight lines in the Formulas of the invention, it is understood that both the (R) and (S) configurations of the chiral carbon, and hence both enantiomers and mixtures thereof, are embraced within the Formula. For example, Formula I shows the structure of the class of compounds without specific stereochemistry. When the compounds of the present invention contain one chiral center, the term "stereoisomer" includes both enantiomers and mixtures of enantiomers, such as the specific 50:50 mixture referred to as a racemic mixtures.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-8}$ alkyl specifically includes methyl, ethyl, n-propyl, iso-propyl, n-butyl, iso-butyl, tert-butyl, pentyl, and hexyl. A group which is designated as being independently substituted with substituents may be independently substituted with multiple numbers of such substituents. The term "heterocycle" as used herein includes both unsaturated and saturated heterocyclic moieties, wherein the unsaturated heterocyclic moieties (i.e. "heteroaryl") include benzoimidazolyl, benzimidazolonyl, benzofuranyl, benzofurazanyl, benzopyrazolyl, benzothiazolyl, benzotriazolyl, benzothiophenyl, benzoxazepin, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, and N-oxides thereof, and wherein the saturated heterocyclic moieties include azetidinyl, 1,4-dioxanyl, hexahydroazepinyl, piperazinyl, piperidinyl, pyridin-2-onyl, pyrrolidinyl, morpholinyl, tetrahydrofuranyl, thiomorpholinyl, and tetrahydrothienyl, and N-oxides thereof.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which selected from the group consisting of the compounds disclosed in the following Examples and pharmaceutically acceptable salts thereof and individual enantiomers or diastereomers thereof.

The subject compounds are useful in a method of antagonizing orexin receptor activity in a patient such as a mammal in need of such inhibition comprising the administration of an effective amount of the compound. The present invention is directed to the use of the compounds disclosed herein as antagonists of orexin receptor activity. In addition to primates, especially humans, a variety of other mammals can be treated according to the method of the present invention. The present invention is directed to a compound of the present invention or a pharmaceutically acceptable salt thereof for use in medicine. The present invention is further directed to a use of a compound of the present invention or a pharmaceutically acceptable salt thereof for the manufacture of a medicament for antagonizing orexin receptor activity or treating the disorders and diseases noted herein in humans and animals.

The subject treated in the present methods is generally a mammal, such as a human being, male or female. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with the disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder. The terms "administration of" and or "administering a" compound should be understood to mean providing a compound of the invention or a prodrug of a compound of the invention to the individual in need thereof.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as orexin receptor OX1R and/or OX2R antagonists may be readily determined without undue experimentation by methodology well known in the art, including the "FLIPR $Ca^{2+}$ Flux Assay" (Okumura et al., Biochem. Biophys. Res. Comm. 280:976-981, 2001). In a typical experiment the OX1 and OX2 receptor antagonistic activity of the compounds of the present invention was determined in accordance with the following experimental method. For intracellular calcium measurements, Chinese hamster ovary (CHO) cells expressing the rat orexin-1 receptor or the human orexin-2 receptor, are grown in Iscove's modified DMEM containing 2 mM L-glutamine, 0.5 g/ml G418, 1% hypoxanthine-thymidine supplement, 100 U/ml penicillin, 100 ug/ml streptomycin and 10% heat-inactivated fetal calf serum (FCS). The cells are seeded at 20,000 cells/well into Becton-Dickinson black 384-well clear bottom sterile plates coated with poly-D-lysine. All reagents were from GIBCO-Invitrogen Corp. The seeded plates are incubated overnight at 37° C. and 5% $CO_2$. Ala-6,12 human orexin-A as the agonist is prepared as a 1 mM stock solution in 1% bovine serum albumin (BSA) and diluted in assay buffer (HBSS containing 20 mM HEPES, 0.1% BSA and 2.5 mM probenecid, pH7.4) for use in the assay at a final concentration of 70 pM. Test compounds are prepared as 10 mM stock solution in DMSO, then diluted in 384-well plates, first in DMSO, then assay buffer. On the day of the assay, cells are washed 3 times with 100 ul assay buffer and then incubated for 60 min (37° C., 5% $CO_2$) in 60 ul assay buffer containing 1 uM Fluo-4AM ester, 0.02% pluronic acid, and 1% BSA. The dye loading solution is then aspirated and cells are washed 3 times with 100 ul assay buffer. 30 ul of that same buffer is left in each well. Within the Fluorescent Imaging Plate Reader (FLIPR, Molecular Devices), test compounds are added to the plate in a volume of 25 ul, incubated for 5 min and finally 25 ul of agonist is added. Fluorescence is measured for each well at 1 second intervals for 5 minutes and the height of each fluorescence peak is compared to the height of the fluorescence peak induced by 70 pM Ala-6,12 orexin-A with buffer in place of antagonist. For each antagonist, IC50 value (the concentration of compound needed to inhibit 50% of the agonist response) is determined. Alternatively, compound potency can be assessed by a radioligand binding assay (described in Bergman et. al. Bioorg. Med. Chem. Lett. 2008, 18, 1425-1430) in which the inhibition constant ($K_i$) is determined in membranes prepared from CHO cells expressing either the OX1 or OX2 receptor. The intrinsic orexin receptor antagonist activity of a compound which may be used in the present invention may be determined by these assays.

In particular, the compounds of the following examples had activity in antagonizing the rat orexin-1 receptor and/or the human orexin-2 receptor in the aforementioned assays, generally with an $IC_{50}$ of less than about 50 μM. Many of compounds within the present invention had activity in antagonizing the rat orexin-1 receptor and/or the human orexin-2 receptor in the aforementioned assays with an $IC_{50}$ of less than about 100 nM. Compounds of the present invention also have activity in the radioligand binding assay, generally with a Ki<100 nM against the orexin-1 and/or the orexin-2 receptor. Additional data is provided in Table 2. Such a result is indicative of the intrinsic activity of the compounds in use as antagonists of orexin-1 receptor and/or the orexin-2 receptor. The present invention also includes compounds within the generic scope of the invention which possess activity as agonists of the orexin-1 receptor and/or the orexin-2 receptor. With respect to other piperidine compounds, the present compounds exhibit unexpected properties, such as with respect to increased potency, oral bioavailability, metabolic stability, and/or selectivity. For example, relative to compounds which possess an unsubstituted piperidine ring, the present compounds wherein $R^3$ is substituted such as with a $C_{1-6}$ alkyl or $C_{3-6}$ cycloalkyl possess unexpectedly greater potency at the orexin-1 receptor and/or the orexin-2 receptor.

The orexin receptors have been implicated in a wide range of biological functions. This has suggested a potential role for these receptors in a variety of disease processes in humans or other species. The compounds of the present invention have utility in treating, preventing, ameliorating, controlling or reducing the risk of a variety of neurological and psychiatric disorders associated with orexin receptors, including one or more of the following conditions or diseases: sleep disorders, sleep disturbances, including enhancing sleep quality, improving sleep quality, increasing sleep efficiency, augmenting sleep maintenance; increasing the value which is calculated from the time that a subject sleeps divided by the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent wakings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia, hypersomnia, idiopathic hypersomnia, repeatability hypersomnia, intrinsic hypersomnia, narcolepsy, interrupted sleep, sleep apnea, wakefulness, nocturnal myoclonus, REM sleep interruptions, jet-lag, shift workers' sleep disturbances, dyssomnias, night terror, insomnias associated with depression, emotional/mood disorders, Alzheimer's disease or cognitive impairment, as well as sleep walking and enuresis, and sleep disorders which accompany aging; Alzheimer's sundowning; conditions associated with circadian rhythmicity as well as mental and physical disorders associated with travel across time zones and with rotating shift-work schedules, conditions due to drugs which cause reductions in REM sleep as a side effect; fibromyalgia; syndromes which are manifested by non-restorative sleep and muscle pain or sleep apnea which is associated with respiratory disturbances during sleep; conditions which result from a diminished quality of sleep; increasing learning; augmenting memory; increasing retention of memory; eating disorders associated with excessive food intake and complications associated therewith, compulsive eating disorders, obesity (due to any cause, whether genetic or environmental), obesity-related disorders including overeating and bulimia nervosa, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia, metabolic syndrome, also known as syndrome X, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, such as obesity-related gastro-esophageal reflux, respiratory disorders, such as obesity-hypoventilation syndrome (Pickwickian syndrome), breathlessness, cardiovascular disorders, inflammation, such as systemic inflammation of the vasculature, arteriosclerosis, hypercholesterolemia, hyperuricaemia, lower back pain, gallbladder disease, gout, kidney cancer, increased anesthetic risk, reducing the risk of secondary outcomes of obesity, such as reducing the risk of left ventricular hypertrophy; diseases or disorders where abnormal oscillatory activity occurs in the brain, including depression, migraine, neuropathic pain, Parkinson's disease, psychosis and schizophrenia, as well as diseases or disorders where there is abnormal coupling of activity, particularly through the thalamus; enhancing cognitive function; enhancing memory; increasing memory retention; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer; cardiac arrhythmia; hypertension; congestive heart failure; conditions of the genital/urinary system; disorders of sexual function and fertility; adequacy of renal function; responsivity to anesthetics; mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; substance-related disorders and addictive behaviors (including substance-induced delirium, persisting dementia, persisting amnestic disorder, psychotic disorder or anxiety disorder; tolerance, addictive feeding, dependence or withdrawal from substances including alcohol, amphetamines, cannabis, cocaine, hallucinogens, inhalants, nicotine, opioids, phencyclidine, sedatives, hypnotics or anxiolytics); movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); attention deficit/hyperactivity disorder (ADHD); conduct disorder; migraine (including migraine headache); urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache.

Thus, in specific embodiments the present invention provides methods for: enhancing the quality of sleep; augmenting sleep maintenance; increasing REM sleep; increasing stage 2 sleep; decreasing fragmentation of sleep patterns; treating insomnia; enhancing cognition; increasing memory retention; treating or controlling obesity; treating or controlling depression; treating, controlling, ameliorating or reducing the risk of epilepsy, including absence epilepsy; treating or controlling pain, including neuropathic pain; treating or controlling Parkinson's disease; treating or controlling psychosis; or treating, controlling, ameliorating or reducing the risk of schizophrenia, in a mammalian patient in need thereof which comprises administering to the patient a therapeutically effective amount of a compound of the present invention.

The subject compounds are further useful in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.0001 to 10 mg/kg. of body weight daily are administered to the patient, e.g., humans and elderly humans, to obtain effective antagonism of orexin receptors. The dosage range will generally be about 0.5 mg to 1.0 g. per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is contemplated. However, the combination therapy may also includes therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is contemplated. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be administered in combination with other compounds which are known in the art to be useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the subject compound may be employed in combination with other compounds which are known in the art, either administered separately or in the same pharmaceutical compositions, include, but are not limited to: insulin sensitizers including (i) PPARγ antagonists such as glitazones (e.g. ciglitazone; darglitazone; englitazone; isaglitazone (MCC-555); pioglitazone; rosiglitazone; troglitazone; tularik; BRL49653; CLX-0921; 5-BTZD), GW-0207, LG-100641, and LY-300512, and the like); (iii) biguanides such as metformin and phenformin; (b) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)-NH$_2$); (c) sulfonylureas, such as acetohexamide; chlorpropamide; diabinese; glibenclamide; glipizide; glyburide; glimepiride; gliclazide; glipentide; gliquidone; glisolamide; tolazamide; and tolbutamide; (d) α-glucosidase inhibitors, such as acarbose, adiposine; camiglibose; emiglitate; miglitol; voglibose; pradimicin-Q; salbostatin; CKD-711; MDL-25,637; MDL-73,945; and MOR 14, and the like; (e) cholesterol lowering agents such as (i) HMG-CoA reductase inhibitors (atorvastatin, itavastatin, fluvastatin, lovastatin, pravastatin, rivastatin, rosuvastatin, simvastatin, and other statins), (ii) bile acid absorbers/sequestrants, such as cholestyramine, colestipol, dialkylaminoalkyl derivatives of a cross-linked dextran; Colestid®; LoCholest®, and the like, (ii) nicotinyl alcohol, nicotinic acid or a salt thereof, (iii) proliferator-activater receptor α agonists such as fenofibric acid derivatives (gemfibrozil, clofibrate, fenofibrate and benzafibrate), (iv) inhibitors of cholesterol absorption such as stanol esters, beta-sitosterol, sterol glycosides such as tiqueside; and azetidinones such as ezetimibe, and the like, and (acyl CoA:cholesterol acyltransferase (ACAT)) inhibitors such as avasimibe, and melinamide, (v) anti-oxidants, such as probucol, (vi) vitamin E, and (vii) thyromimetics; (f) PPARα agonists such as beclofibrate, benzafibrate, ciprofibrate, clofibrate, etofibrate, fenofibrate, and gemfibrozil; and other fibric acid derivatives, such as Atromid®, Lopid® and Tricor®, and the like, and PPARα agonists as described in WO 97/36579 by Glaxo; (g) PPARδ agonists; (h) PPAR α/δ agonists, such as muraglitazar, and the compounds disclosed in U.S. Pat. No. 6,414,002; and (i) anti-obesity agents, such as (1) growth hormone secretagogues, growth hormone secretagogue receptor agonists/antagonists, such as NN703, hexarelin, MK-0677, SM-130686, CP-424,391, L-692,429, and L-163,255; (2) protein tyrosine phosphatase-1B (PTP-1B) inhibitors; (3) cannabinoid receptor ligands, such as cannabinoid CB$_1$ receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer); (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A; (6) pancreatic lipase inhibitors, such as orlistat (Xenical®), Triton WR1339, RHC80267, lipstatin, tetrahydrolipstatin, teasaponin, diethylumbelliferyl phosphate; (7) neuropeptide Y1 antagonists, such as BIBP3226, J-115814, BIBO 3304, LY-357897, CP-671906, GI-264879A; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104; (9) melanin-concentrating hormone (MCH) receptor antagonists; (10) melanin-concentrating hormone 1 receptor (MCH1R) antagonists, such as T-226296 (Takeda); (11) melanin-concentrating hormone 2 receptor (MCH2R) agonist/antagonists; (12) orexin receptor antagonists, such as SB-334867-A, and those disclosed in patent publications herein; (13) serotonin reuptake inhibitors such as fluoxetine, paroxetine, and sertraline; (14) melanocortin agonists, such as Melanotan II; (15) other Mc4r (melanocortin 4 receptor) agonists, such as CHIR86036 (Chiron), ME-10142, and ME-10145 (Melacure), CHIR86036 (Chiron); PT-141, and PT-14 (Palatin); (16) 5HT-2 agonists; (17) 5HT2C (serotonin receptor 2C) agonists, such as BVT933, DPCA37215, WAY161503, R-1065; (18) galanin antagonists; (19) CCK agonists; (20) CCK-A (cholecystokinin-A) agonists, such as AR-R 15849, GI 181771, JMV-180, A-71378, A-71623 and SR14613; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and O-[3-(1H-imidazol-4-yl)propanol]-carbamates; (25) β-hydroxy steroid dehydrogenase-1 inhibitors (β-HSD-1); 26) PDE (phosphodiesterase) inhibitors, such as theophylline, pentoxifylline, zaprinast, sildenafil, aminone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists; (30) leptin, including recombinant human leptin (PEG-OB, Hoffman La Roche) and recombinant methionyl human leptin (Amgen); (31) leptin derivatives; (32) BRS3 (bombesin receptor subtype 3) agonists such as [D-Phe6,beta-Ala11,Phe13,Nle14]Bn(6-14) and [D-Phe6,Phe13]Bn(6-13) propylamide, and those compounds disclosed in Pept. Sci. 2002 Aug.; 8(8): 461-75); (33) CNTF (Ciliary neurotrophic factors), such as GI-181771 (Glaxo-SmithKline), SR146131 (Sanofi Synthelabo), butabindide, PD170,292, and PD 149164 (Pfizer); (34) CNTF derivatives, such as axokine (Regeneron); (35) monoamine reuptake inhibitors, such as sibutramine; (36) UCP-1 (uncoupling protein-1), 2, or 3 activators, such as phytanic acid, 4-[(E)-2-(5,6,7,8-tetrahydro-5, 5,8,8-tetramethyl-2-napthalenyl)-1-propenyl]benzoic acid (TTNPB), retinoic acid; (37) thyroid hormone agonists, such as KB-2611 (KaroBioBMS); (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, MK-431, P93/01, TSL 225, TMC-2A/2B/2C, FE 999011, P9310/K364, VIP 0177, SDZ 274-444; (46) dicarboxylate transporter inhibitors; (47) glucose transporter inhibitors; (48) phosphate transporter inhibitors; (49) Metformin (Glucophage®); and (50) Topiramate (Topimax®); and (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999)); (51) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (52) Neuropeptide Y4 (NPY4) agonists such as pancreatic peptide (PP), and other Y4 agonists such as 1229U91; (54) cyclooxygenase-2 inhibitors such as etoricoxib, celecoxib, valdecoxib, parecoxib, lumiracoxib, BMS347070, tiracoxib or JTE522, ABT963, CS502 and GW406381, and pharmaceutically acceptable salts thereof; (55) Neuropeptide Y1 (NPY1) antagonists such as BIBP3226, J-115814, BIBO 3304, LY-357897, CP-671906, GI-264879A; (56) Opioid antagonists such as nalmefene (Revex®), 3-methoxynaltrexone, naloxone, naltrexone; (57) 11β HSD-1 (11-beta hydroxy steroid dehydrogenase type 1) inhibitor such as BVT 3498, BVT 2733; (58) a minorex; (59) amphechloral; (60) amphetamine; (61) benzphetamine; (62) chlorphentermine; (63) clobenzorex; (64) cloforex; (65) clominorex; (66) clortermine; (67) cyclexedrine; (68) dextroamphetamine; (69) diphemethoxidine, (70) N-ethylamphetamine; (71) fenbutrazate; (72) fenisorex; (73) fenproporex; (74) fludorex; (75) fluminorex; (76) furfurylmethylamphetamine; (77) levamfetamine; (78) levophacetoperane; (79) mefenorex; (80) metamfepramone; (81) methamphetamine; (82) norpseudoephedrine; (83) pentorex; (84) phendimetrazine; (85) phenmetrazine; (86) picilorex; (87) phytopharm 57; and (88) zonisamide.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-$HT_{1A}$ agonists or antagonists, especially 5-$HT_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the subject compound may be employed in combination with anti-Alzheimer's agents; beta-secretase inhibitors; gamma-secretase inhibitors; growth hormone secretagogues; recombinant growth hormone; HMG-CoA reductase inhibitors; NSAID's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine $H_3$ antagonists; AMPA agonists; PDE IV inhibitors; GABAA inverse agonists; or neuronal nicotinic agonists.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amitriptyline, amobarbital, amoxapine, bentazepam, benzoctamine, brotizolam, bupropion, busprione, butabarbital, butalbital, capuride, carbocloral, chloral betaine, chloral hydrate, chlordiazepoxide, clomipramine, clonazepam, cloperidone, clorazepate, clorethate, clozapine, cyprazepam, desipramine, dexclamol, diazepam, dichloralphenazone, divalproex, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, venlafaxine, zaleplon, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexyl)hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with acetophenazine, alentemol, benzhexyl, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene or trifluoperazine.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form.

In another embodiment, the subject compound may be employed in combination with an anoretic agent such as aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; selective serotonin reuptake inhibitor (SSRI); halogenated amphetamine derivatives, including chlorphentermine, cloforex, clortermine, dexfenfluramine, fenfluramine, picilorex and sibutramine; and pharmaceutically acceptble salts thereof.

In another embodiment, the subject compound may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art or as illustrated herein. The following abbreviations are used herein: Me: methyl; Et: ethyl; t-Bu: tert-butyl; Ar: aryl; Ph: phenyl; Bn: benzyl; Ac: acetyl; THF: tetrahydrofuran; DEAD: diethylazodicarboxylate; DIPEA: N,N-diisopropylethylamine; DMSO: dimethylsulfoxide; EDC: N-(3-Dimethylaminopropyl)-N'-ethylcarbodiimide; HOBT: hydroxybenzotriazole hydrate; Boc: tert-butyloxy carbonyl; $Et_3N$: triethylamine; DCM: dichloromethane; DCE: dichloroethane; BSA: bovine serum albumin; TFA: trifluoracetic acid; DMF: N,N-dimethylformamide; MTBE: methyl tert-butyl ether; $SOCl_2$: thionyl chloride; CDI: carbonyl diimidazole; rt: room temperature; HPLC: high performance liquid chromatography; T3P: 1-propylphosphonic anhydride. The compounds of the present invention can be prepared in a variety of fashions.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes and examples may be varied to facilitate the reaction or to avoid unwanted reaction products. The following examples are provided so that the invention might be more fully understood. These examples are illustrative only and should not be construed as limiting the invention in any way.

EXAMPLE A

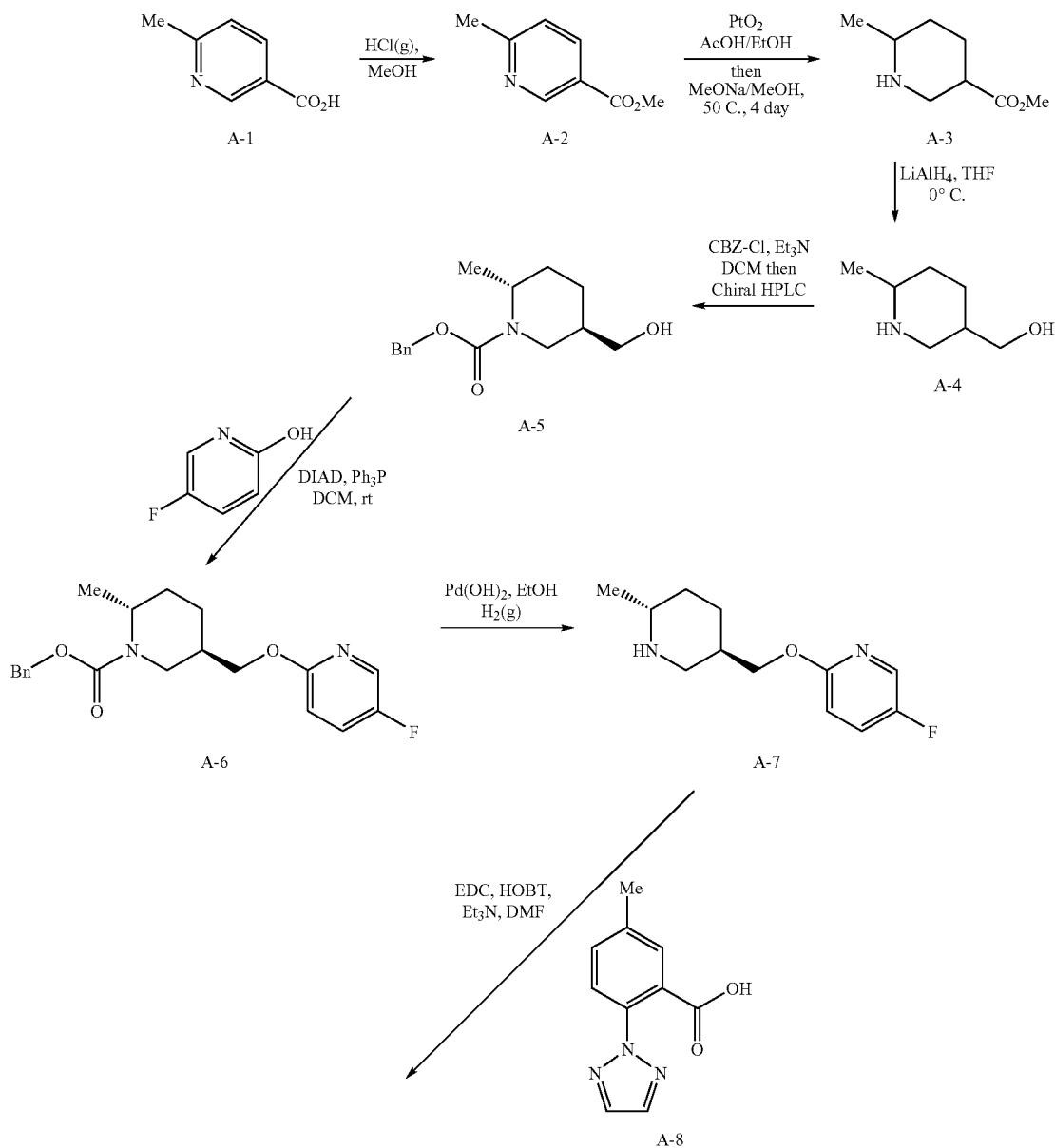

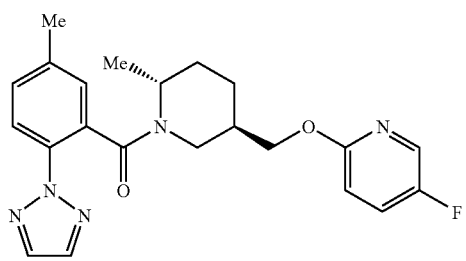

A-9

6-Methylnicotinic acid methyl ester (A-2)

A solution of 6-methylnicotinic acid (20 g, 146 mmol) in MeOH (300 ml) was treated with HCl gas until the solvent was saturated. The reaction was capped and stirred for 1.5 h at RT. The mixture was treated again with HCl gas until the solvent was saturated and was capped and stirred overnight at 22° C. The solution was concentrated to yield A-2. Data for A-2: LRMS m/z (M+H): 152.75.

6-Methyl-3-piperidinecarboxylic acid methyl ester (A-3)

A solution of the A-2 (23 g, 152 mmol) in EtOH (200 ml) was treated with 5 mol % platinum oxide (1.728 g, 7.61 mmol) and acetic acid (8.71 ml, 152 mmol). The Parr bottle was evacuated and backfilled with $H_2$ (g) three times and stirred under a $H_2$ (g) atmosphere (45 psi, recharged 4 times) at 22° C. for 3 h. The mixture was filtered though Celite and the filter cake was washed with MeOH. The filtrate was concentrated to yield product with a ~3.5:1 cis:trans diastereomer ratio. This material was diluted with 300 mL MeOH, treated with sodium methoxide (32.9 g, 183 mmol), heated to 50° C., and stirred at this temp for 4 days. The mixture was cooled to 22° C., neutralized to pH 7 with conc. HCl, filtered through celite and the filtrate was concentrated. The residue was suspended in MeOH and filtered again. The resulting filtrate was concentrated to yield A-3 (~3:1 trans:cis). Data for A-3: LRMS m/z (M+H): 158.9.

6-Methyl-3-piperidinemethanol (A-4)

A suspension of the amine hydrochloride, ~3:1 trans:cis (500 mg, 2.58 mmol) in THF (15 ml) was treated slowly with lithium aluminum hydride (3.37 ml, 7.75 mmol) at 22° C. The solution was warmed to 0° C. and stirred for 20 min, then treated dropwise with 0.294 mL of water, 0.294 ml of 15% NaOH, and 0.882 mL of water successively. Sodium sulfate was added to the mixture. After stirring 20 min at 22° C., the mixture was filtered and the filtrate was concentrated to yield A-4. as a colorless oil. Data for A-4: LRMS m/z (M+H): 130.2.

Benzyl (2R,5R)-5-(hydroxymethyl)-2-methylpiperidine-1-carboxylate (A-5)

A solution of the amine A-4 (350 mg, 2.71 mmol) in DCM (15 ml) was treated with TEA (0.755 ml, 5.42 mmol) and CBZ-Cl (0.387 ml, 2.71 mmol). The mixture was stirred at 22° C. and concentrated. The residue was partitioned between EtOAc and water. The organic phase was dried over $Na_2SO_4$, filtered and concentrated. The crude material was purified by gradient elution on silica gel (0 to 70% EtOAc in Hex) to yield 377 mg of racemic material (~3:1 trans:cis). The trans material was separated away from the cis diastereomers and into its enantiomers on a 5 cm OD chiral column by isocratic elution (93:7 Hexane:EtOH; 75 mL/min; 1 inj) with detection at 215 nm to yield 120 mg of A-5, peak 1 (colorless oil, 100% ee) and 114 mg of peak 2. (colorless oil, contaminated with 30% cis, 90% ee). Data for A-5: LRMS m/z (M+H): 264. Similarly, the cis diastereomer can be separated into its enantiomers and utilized in the following procedures to prepare (R,S) and (S,R) compounds.

Benzyl (2R,5R)-5-{[(5-fluoropyridin-2-yl)oxy]methyl}-2-methylpiperidine-1-carboxylate (A-6)

A solution of the first-eluting isomer A-5 (120 mg, 0.456 mmol), 5-fluoro-2-hydroxypyridine (56.7 mg, 0.501 mmol), and resin bound-triphenylphosphine (0.254 ml, 0.547 mmol) in DCM (3 ml) was treated with diisopropylazadicarboxylate (0.106 ml, 0.547 mmol). The mixture was stirred overnight, filtered and the filtrated concentrated. The crude material was purified by gradient elution on reverse phase (5 to 95% MeCN in water (0.1% TFA)) to give pure fractions which were concentrated, diluted with EtOAc and washed with sat. aq. $NaHCO_3$. The organic phase was dried over $Na_2SO_4$, filtered and concentrated to yield A-6 as a colorless film. Data for A-6: LRMS m/z (M+H): 264.

5-Fluoro-2-{[(3R,6R)-6-methylpiperidin-3-yl]methoxy}pyridine (A-7)

A solution of the carbamate A-6 (107 mg, 0.299 mmol) in EtOH (5 ml) was treated with 10 mol % palladium hydroxide on carbon (20.96 mg, 0.030 mmol). The flask was evacuated and backfilled with $H_2$ (g) three times and stirred under a $H_2$ (g) atmosphere (1 atm) at 22° C. for 40 m. The mixture was filtered though a syringe filter. The filtrate was concentrated to yield A-7 as a colorless film. Data for A-7: LRMS m/z (M+H): 225.

2-(2H-1,2,3-Triazol-2-yl)-5-methylbenzoic acid (A-8)

A solution of 2-iodo-5-methylbenzoic acid (4.0 g, 15.3 mmol) in DMF (10 mL) was treated with 1,2,3-triazole (2.1 g, 30.5 mmol), $Cs_2CO_3$ (9.95 g, 30.5 mmol), CuI (0.145 g, 0.76 mmol) and trans-N,N'-dimethylcyclohexane-1,2-diamine (0.43 g, 3.05 mmol). The mixture was heated at 120° C. for 10 min in a microwave reactor. The reaction was cooled to room temperature, diluted with water, and washed with EtOAc. The aqueous phase was acidified with 1N HCl and extracted with EtOAc. The organic layer was dried over $Na_2SO_4$, filtered and concentrated. The residue was purified by gradient elution on SiO$_2$ (0 to 10% MeOH in CH$_2$Cl$_2$ with 0.1% AcOH) to give the faster eluting 2-(2H-1,2,3-triazol-2-yl)-5-methylbenzoic acid A-8, followed by the undesired regioisomer isomer, 1-(2H-1,2,3-triazol-2-yl)-5-methylbenzoic acid. Data for A-8: $^1$HNMR (500 MHz, DMSO-d$_6$) δ 12.98 (br s, 1H), 8.04 (s, 2H), 7.72-7.45 (m, 3H), 2.41 (s, 3H) ppm.

5-Fluoro-2-({(3R,6R)-6-methyl-1-[5-methyl-2-(2H-1,2,3-triazol-2-yl)benzoyl]piperidin-3-yl}methoxy)pyridine (A-9)

A solution of A-7 (67 mg, 0.299 mmol) in DMF (1 ml) was treated with acid A-8 (60.7 mg, 0.299 mmol), EDC (68.7 mg, 0.358 mmol), HOBT (54.9 mg, 0.358 mmol), and triethylamine (0.167 ml, 1.195 mmol). After stirring at 22° C. overnight, the mixture was diluted with EtOAc and washed with water three times. The organic phase was dried over Na$_2$SO$_4$, filtered and concentrated. The crude material was purified by gradient elution on silica gel (0 to 75% EtOAc in Hex) to yield impure material. This material was purified by gradient elution on reverse phase (5 to 95% MeCN in water (0.1% TFA) to give pure fractions which were concentrated, diluted with EtOAc and washed with sat. aq. NaHCO$_3$. The organic phase was dried over Na$_2$SO$_4$, filtered and concentrated to yield A-9 as a white solid. Data for A-9: HRMS m/z (M+H): 410.1993, found. 410.1987, required.

EXAMPLE B mmol) followed by C-1 (447 mg, 1.6 mmol, generated from A-8 by treatment with SOCl$_2$ and catalytic DMF in CH$_2$Cl$_2$). After warming to room temperature and stirring for 2 h, the reaction was partitioned between CH$_2$Cl$_2$ and saturated aqueous NaHCO$_3$. The layers were separated, the aqueous was extracted again with CH$_2$Cl$_2$, the combined organics were washed with water, dried over Na$_2$SO$_4$, filtered and concentrated. The crude material was purified by gradient elution on silica gel (0 to 100% EtOAc in Hex) to yield 530 mg of B-2 as a white solid. Data for B-2: LRMS m/z (M+H): 469.1.

2-{2-[((2R,5R)-5-{[(5-Fluoropyridin-2-yl)oxy]methyl}-2-methylpiperidin-1-yl)carbonyl]-4-methylphenyl}pyrazine (B-3)

To a solution of B-2 (70 mg, 0.15 mmol) in DMF (2 ml) at was added 2-tributylstannylpyrazine (83 mg, 0.22 mmol), copper(I) iodide (5.7 mg, 0.03 mmol), cesium fluoride (45 mg, 0.3 mmol), and tetrakistriphenylphospinepalladium(0) (17 mg, 0.015 mmol). After stirring at 80° C. overnight, the reaction was partitioned between EtOAc and saturated aqueous NaHCO$_3$. The layers were separated, the organic was washed with water, saturated brine, dried over MgSO$_4$, filtered and concentrated. The crude material was purified by gradient elution on silica gel (0 to 100% EtOAc in Hex), followed by a second chromatography on silica gel (0 to 100% 80:10:10 CHCl$_3$:EtOAc:MeOH in CHCl$_3$) to yield 20 mg of B-3 as a colorless gum. Data for B-3: HRMS m/z (M+H): 421.2011, found. 421.2034, required.

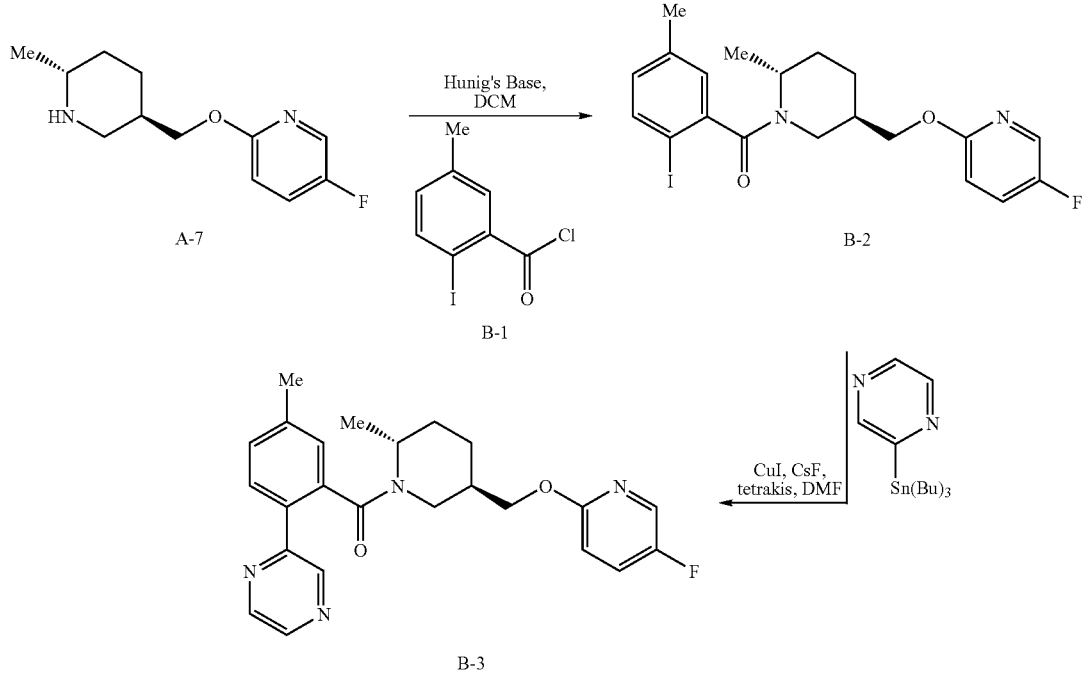

5-Fluoro-2-{[(3R,6R)-1-(2-iodo-5-methylbenzoyl)-6-methylpiperidin-3-yl]methoxy}pyridine (B-2)

To a solution of A-7 (325 mg, 1.5 mmol) in CH$_2$Cl$_2$ (50 ml) at 0° C. was added diisopropylethylamine (506 mL, 2.9

EXAMPLE C

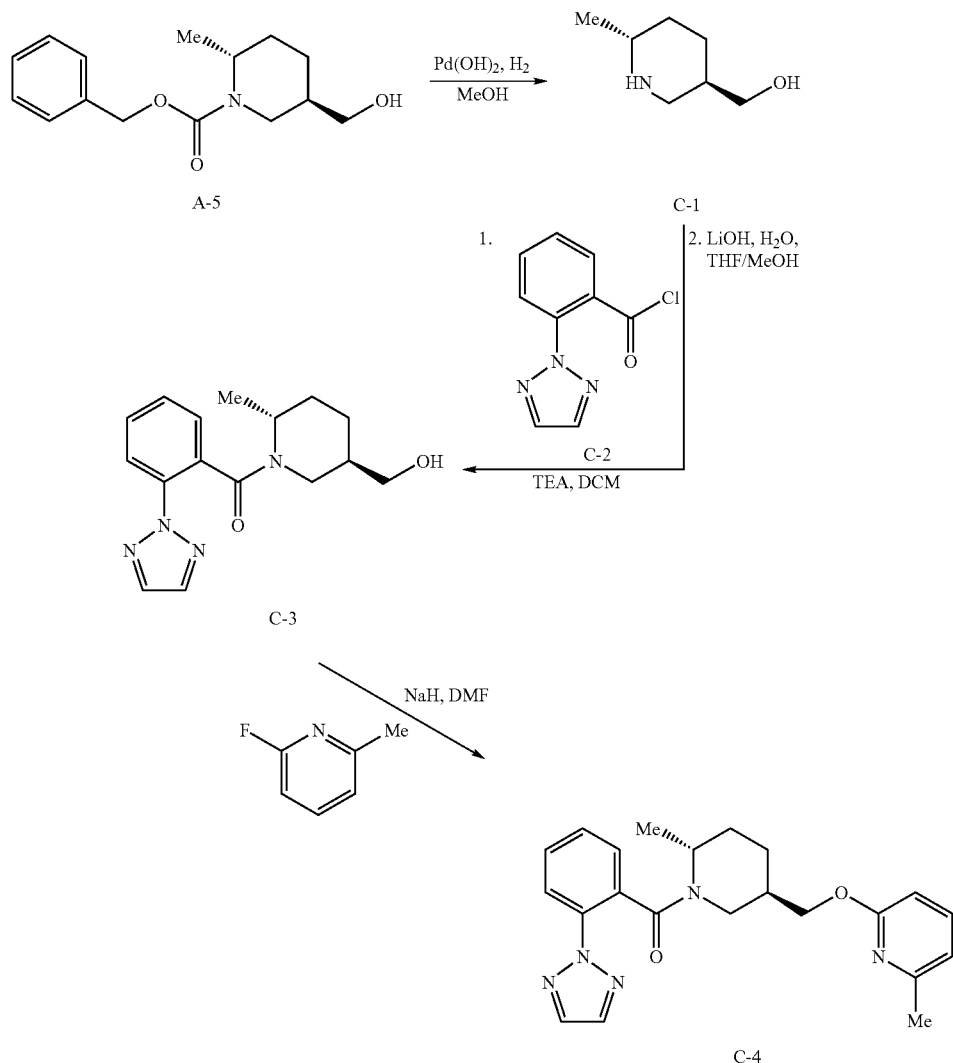

[(3R,6R)-6-methylpiperidin-3-yl]methanol (C-1)

To a solution of A-5 (2.75 g, 10.4 mmol) in MeOH (50 mL) was added 20% Pd(OH)₂ on carbon (~700 mg), the flask was evacuated and the atmosphere replaced with H₂. After stirring under a balloon of H₂ overnight, the reaction was filtered through Celite and concentrated to provide 1.29 g (96%) of C-1 as a white solid. Data for C-1: LRMS m/z (M+H): 130.2.

{(3R,6R)-6-Methyl-1-[2-(2H-1,2,3-triazol-2-yl)benzoyl]piperidin-3-yl}methanol (C-3)

To a solution of C-1 (675 mg, 5.22 mmol) in CH₂Cl₂ (70 ml) at 0° C. was added triethylamine (2.9 mL, 20.9 mmol) followed by C-2 (2.17 g, 10.4 mmol, synthesized in a similar manner as B-1 starting from 2-iodobenzoic acid). After warming to room temperature and stirring overnight, the reaction was partitioned between CH₂Cl₂ and water. The layers were separated, the organic was washed with saturated aqueous NaHCO₃, water, dried over Na₂SO₄, filtered and concentrated to provide 2.46 g of a tan solid that is bis-acylated material. To hydrolyze the ester selectively, this material was dissolved in 150 mL of 1:1 THF/MeOH and to this was added 50 mL of 1M LiOH. After stirring overnight at room temperature, the mixture was partitioned between EtOAc and 0.5 M NaOH. The layers were separated, the organic was washed twice with 0.5M NaOH, saturated brine, dried over Na₂SO₄, filtered and concentrated. The crude material was purified by gradient elution on silica gel (0 to 100% EtOAc in Hex) to yield 890 mg of C-3 as a white solid. Data for C-3: LRMS m/z (M+H): 301.2.

2-Methyl-6-({(3R,6R)-6-methyl-1-[2-(2H-1,2,3-triazol-2-yl)benzoyl]piperidin-3-yl}methoxy)pyridine (C-4)

To a solution of C-3 (50 mg, 0.25 mmol) in DMF (2 ml) was added sodium hydride (10 mg, 0.25 mmol, 60% suspension in oil) followed by 2-fluoro-6-methylpyridine (21 mg, 0.18 mmol). After stirring at room temperature overnight, an additional portion of NaH and 2-fluoro-6-methylpyridine were added, and stirring was continued for 8 h more until being quenched with saturated aqueous NH₄Cl. The mixture was then partitioned between EtOAc and saturated aqueous NaHCO₃. The layers were separated, the organic was washed with water, saturated brine, dried over MgSO₄, filtered and concentrated. The crude material was purified by gradient elution on silica gel (0 to 100% EtOAc in Hex) to yield 70 mg of C-4 as a white solid. Data for C-4: HRMS m/z (M+H): 392.2059, found. 392.2081, required.

EXAMPLE D

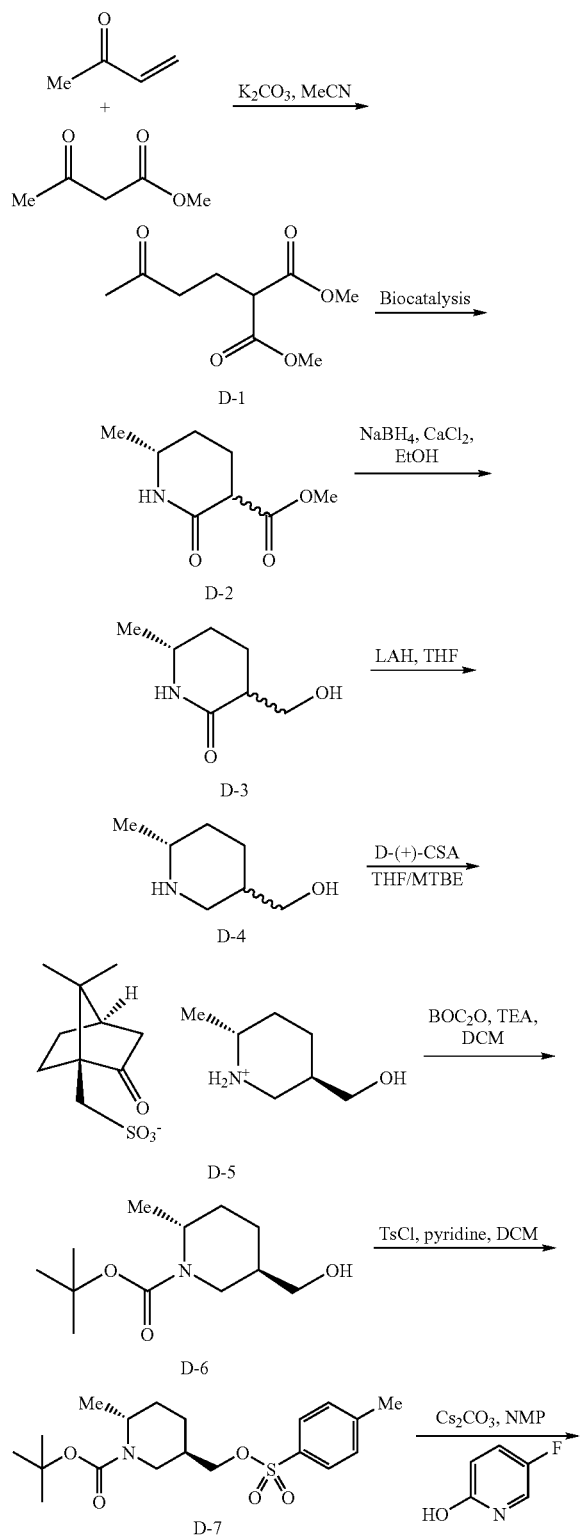

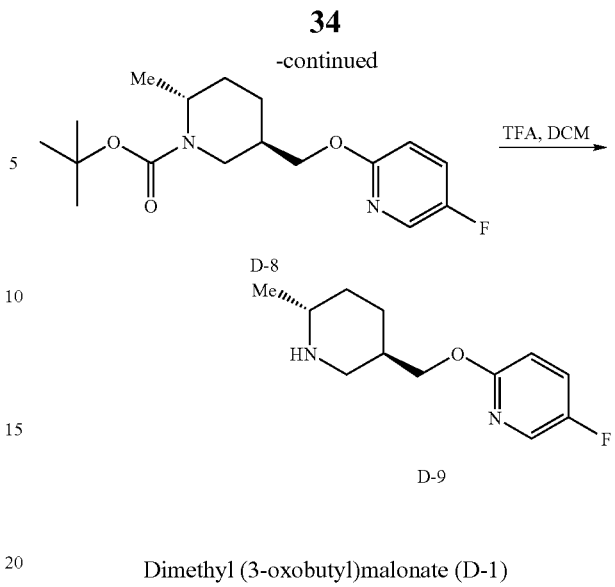

Dimethyl (3-oxobutyl)malonate (D-1)

To a visually clean and dry 100 L round bottom flask equipped with an addition funnel, a nitrogen inlet and a thermocouple was added acetonitrile and potassium carbonate. Dimethyl malonate was added and the resulting mixture was cooled to 17° C. (ice/water bath). The methyl vinyl ketone was added over 3 h with the internal temperature not rising above 26° C. After 18 h, HPLC showed full conversion. The mixture was transferred to a 100 L extractor charged with 60 L MTBE and 20 L water. The layers were separated and the aqueous layer was back extracted with 20 L MTBE. The combined organic layers were washed with 20 L water, allowing 5 h for the emulsion to settle. The organic layer was then filtered through solka floc and batch concentrated, flushing with 20 L MTBE to afford 15.1 kg of D-1 (80 wt % by $^1$H NMR, 80% yield). Data for D-1: $^1$H NMR (400 MHz, CDCl$_3$) δ 3.69 (s, 6H), 3.40 (t, J=7.3 Hz, 1H), 2.50 (t, J=7.2 Hz, 2H), 2.15-2.06 (m, 5H).

Methyl (6R)-6-methyl-2-oxopiperidine-3-carboxylate (D-2)

To a visually clean 20 L round bottom flask was charged 7.15 kg of 64 wt % D-1 and rotavaped to remove residual acetonitrile and MTBE. Resulting solution is 83 wt %. To a visually clean 100 L Buchi jacketed reactor with overhead stirring was added 45 L water. Heating to 30° C. was initiated, followed by addition of 852 g Na$_2$HPO$_4$, 7.2 kg D-alanine, 6.48 kg Glucose, 22.5 g NAD, and 45 g PLP. The pH was adjusted to 7.4 with NaOH and then 450 g ATA-117 transaminase, 9 g Lactate Dehydrogenase, and 45 g glucose dehydrogenase were added and rinsed into the vessel with 2.5 L water. After all enzymes were in solution, the rotavaped solution of D-1 was added, followed by a final 2.5 L water. pH control utilizing 5 N NaOH was initiated. The reaction was allowed to stir for 42 hours; reaction was complete at 31 hours. To the reaction vessel was added 19.4 kg NaCl and 6.0 L 5N HCl to adjust the pH to 3.5. 20 L of acetonitrile was added and allowed to stir for 10 min. The agitator was turned off and the reaction mixture allowed to settle for 1 hr. The acetonitrile layer was drummed off; the aqueous layer was re-extracted with acetonitrile, and these acetonitrile layers were combined. The resulting acetonitrile solution was filtered through Solka-floc and combined with a second batch of similar size and batch concentrated to remove both acetonitrile and water. The resulting oil contained high levels of heterogeneous NaCl. The oil was then dissolved in 50 L EtOAc and transferred to a visually clean 20 L round bottom flask and rotavaped to provide D-2 as an oil (5.5 kg, 94 wt %, 74% yield, 99% ee determined by HPLC on Chiralpak). Data for D-2: LRMS (M+H)=172

(6R)-3-(Hydroxymethyl)-6-methylpiperidin-2-one (D-3)

A visually clean and dry 140 L extractor, equipped with glycol cooling coils, nitrogen inlet, large gas exit and thermocouple was charged with an 18.7 wt % solution of D-2 in EtOH [4.6 L/kg] and an additional 71.4 L EtOH [25.4 L/kg]. Calcium chloride was added in 3 portions over 15 min and stirred until complete dissolution with cooling from 26 to 22° C. Sodium borohydride was added in 3 portions over 20 min. After last addition, temperature increases to 25° C. Gas evolution subsided within 30 min. The reaction mixture was allowed to stir for 20 h with the cooling set to keep the temperature below 22° C. The mixture was cooled to 5° C. and was quenched by careful addition of 11.2 L 6 N HCl over 30 min, keeping the temperature below 9.5° C. It was warmed to room temperature and stirred for 2 h. Wet pH paper dipped in the mixture showed pH 2. It was filtered over Solka floc and rinsed with 2×12 L EtOH. Each bin was assayed for a total of 2.55 kg (108% AY). The filtrate was combined with a second batch of similar size for batch concentration. After most of the ethanol was evaporated, 8 L of water were added to coevaporate EtOH and partially solubilize precipitate. After transferring the 23 L aqueous layer to the extractor, the volume was adjusted with water to 31.6 L. It was extracted with 53 L then 2×26.5 L 1-butanol (HPLC assay shows 92 g, 1.9% losses in the aqueous layer). The combined organic layers were washed with 10.5 L brine (HPLC assay shows 419 g, 8.8% losses to the wash). The organic layer was assayed to 4.21 kg (92% recovery, 96% AY) and concentrated to a minimum volume. It was then azeotroped with 12 L water, then 120 L isopropanol. The KF was assayed to 0.5% water on a total volume of ~40 L. The suspension was filtered over Solka floc and rinsed with 2×10 L isopropanol. The filtrate was stirred in the extractor to homogenize it and was assayed to 4.13 kg (94% AY, 1.7:1 dr). The solution was separated in two equal batches. Each batch was concentrated to a minimum volume and azeotroped with 140 L THF to yield D-3 as a beige suspension. (94% yield). $^1$H NMR shows 0.6 eq isopropanol. Data for D-3: LRMS (M+H)=144

[(6R)-6-methylpiperidin-3-yl]methanol (D-4)

A visually clean and dry 100 L 5-neck round-bottom flask equipped with a mechanical stirrer, a thermocouple, a nitrogen inlet and a cooling bath was charged with D-3 (2.07 kg, 1.0 eq) and THF (20 L, 10 mL/g). The mixture was cooled to −25° C. The LiAlH$_4$ (2.6M soln, 22.2 L, 4.0 eq) was added over a period of 3.5 hrs, keeping the mixture between −25° C. and +12° C. An important gas evolution (H$_2$) was observed during the addition of the first 6 L of LiAlH$_4$. Upon completion of the addition, the mixture was allowed to warm to 20° C., then heated using steam to 50° C. The mixture was aged at this temperature for a period of 12 hrs. GC-FID and LC-MS showed >99% conversion to the desired piperidine-alcohol. The mixture was cooled to −25° C., and the reaction was quenched using the Fieser work-up. Water (2.2 L) was added over 3 hrs to the mixture, creating an important gas evolution and exotherm (temperature was kept between −25° C. and +13° C.). 3.75M NaOH (2.2 L) was then added to the mixture over a period of 1.5 hrs. Finally, water (6.6 L) was added over a period of 1 hr. The mixture was cooled to 5° C. and aged 1.5 hrs. The suspension was filtered, and the cake was rinsed with THF (20 L). 1.54 Kg (2.33% wt) were obtained, therefore the assay yield of D-4 was 82% (dr=1.7:1, favoring the trans isomer). Data for D-4: LRMS (M+H)=130

[(3R,6R)-6-methylpiperidin-3-yl]methanol-CSA salt (D-5)

A visually clean and dry 140 L 5-neck extractor equipped with a mechanical stirrer, a thermocouple, a nitrogen inlet and a cooling coil was charged with D-4 (3.04 Kg, 1.0 eq) and THF (60 L, 20 mL/g). To the mixture was added a THF solution (4 mL/g, 12 L) of (D)-(+)-CSA (4.37 Kg, 0.8 eq) over a period of 1 hr. The salt crystallized out without seeding. Upon completion of the addition, the mixture was aged 45 min at 20° C., then MTBE (10 mL/g, 30 L) was added over 45 min. The mixture was aged for 45 min, then cooled to 2° C. over 45 min. The mixture was aged at this temperature for a period of 30 min, then filtered. The salt was rinsed 2×6 mL/g (2×18 L) with THF/MTBE 1/1, then 1×6 mL/g (1×18 L) MTBE, and was dried on the frit under a nitrogen atmosphere for a period of 16 hrs to provide 4.46 Kg (52%) of D-5 as a white solid. The diastereoselectivity of the salt (measured on a free base sample after salt break) was 40-50:1.

tert-butyl (2R,5R)-5-(hydroxymethyl)-2-methylpiperidine-1-carboxylate (D-6)

A visually clean and dry 140 L extractor, equipped with glycol cooling coils, nitrogen inlet, and thermocouple was charged 40 L of dichloromethane followed by D-5 (4.2 Kg). To this suspension was added triethyamine in one portion (4.8 L, no exotherm observed) followed by Boc$_2$O (2.66 kg added over 5 min, 4° C. exotherm observed). After 30 minutes, the reaction mixture became homogeneous. An LCMS assay (after 3 hr) showed complete consumption of the starting material. The reaction mixture was diluted with ammonium chloride 2 M (40 L) and the layers were separated. The organic layer was washed with half saturated brine (20 L) and the layers were separated. An HPLC assay of the crude reaction mixture indicated a 105% AY (2.81 kg). This crude reaction mixture was dried over Na$_2$SO$_4$ (200 wt %), filtered and transferred into a 100 L flask for the tosylation reaction.

tert-butyl (2R,5R)-2-methyl-5-({[(4-methylphenyl) sulfonyl]oxy}methyl)piperidine-1-carboxylate (D-7)

A visually clean and dry 100 L reactor equipped with a mechanical stirrer, a nitrogen inlet and a thermocouple was charged with the crude dichloromethane solution of D-6 (final volume was adjusted to 10 L, approximately 2.2 mL/g). To this cold solution (0° C.) was added pyridine (5.5 L, no exotherm observed) followed by TsCl (in 4 portion over 1 hr, exotherm observed but easily controlled). The reaction mixture was warmed to room temperature and stirred for 18 hrs (HPLC showed complete consumption of the starting material). The reaction mixture was transferred into a 140 L extractor and diluted with MTBE (7 mL/g), NH$_4$Cl sat. (20 L) and water (10 L). The layers were separated and the organic layer was washed with CuSO$_4$.5H$_2$O (20 L followed by 10 L), NaHCO$_3$ sat (10 L) and half saturated brine (10 L). The crude organic layer was filtered on a pad of silica gel (1.5 kg) and the pad was rinsed with MTBE (10 L). The assay yield of D-7 measured on the resulting solution was 93% (4.28 kg). Data for D-7: LRMS (M-Boc)=284.0 tert-butyl (2R,5R)-5-{[(5-fluoropyridin-2-yl)oxy]methyl}-2-methylpiperidine-1-carboxylate (D-8)

A visually clean and dry 100 L 5-neck round-bottom flask equipped with a mechanical stirrer, a thermocouple, a nitrogen inlet and a cooling bath was charged with D-7 (3.23 Kg, 1.0 eq) and NMP (65 L, 20 mL/g). 5-Fluoro-2-hydroxypyridine (1.19 Kg, 1.25 eq) was added, followed by the addition of the $Cs_2CO_3$ (7.37 Kg, 2.7 eq). No exotherm was observed. The mixture was warmed to 60° C. and aged at this temperature for a period of 26 hrs. HPLC showed >99.9% conversion to the desired product. The mixture was cooled to 15° C., the reaction was quenched by the addition of water (65 L), added over 1 hr to control the exotherm (15° C. to 28° C.). The piperidine-O-pyridine was extracted using MTBE (20 mL/g, 65 L). The organic layer was washed 2×10 mL/g 10% LiCl (2×32 L), then 2×10 mL/g NaCl half saturated solution (2×32 L). The assay yield of D-8, measured on the MTBE layer, was 2.16 Kg, 79%. Data for D-8: HRMS (M+H)=325.1922

5-fluoro-2-{[(3R,6R)-6-methylpiperidin-3-yl]methoxyl}pyridine (D-9)

A visually clean 50 L flask equipped with a thermocouple and mechanical stirrer was charged with a solution of D-8 (2.15 kg, 6.63 mol) in MTBE which was solvent switched to dichloromethane (11.40 L). This mixture was cooled to −2° C. with an ice/IPA bath. TFA (5.5 L, 71.4 mol) was then added slowly (over 40 minutes. T ° C.=−1.9° C. to 5.5° C., max 5.5° C.). Once addition was completed, the reaction was removed from the ice bath and warmed to room temperature with warm water (start 5.7° C., 50 minutes). The reaction was completed within 3.5 hours. Concentration under reduced pressure and transfer of the resulting oil to a cooled stirring solution of NaOH (3.0N, 1.1 eq., 28 L) in a 100 L extractor was followed by addition of 30 L of MTBE and the phases were separated. The organic layer was washed with 30 L of 2N HCl and again with 10 L of 2N HCl. The aqueous layers were then cooled (9° C.) and 10N NaOH was added until the pH was 13 (T°=21° C.). To this solution was added 25 L of MTBE and the layers were cut. Finally, the aqueous layer was back-extracted with 10 L of MTBE. Quantitative HPLC assay revealed 98% yield and >99.7% purity of D-9 used as is a subsequent reaction. Data for D-9: LRMS (M+H)=225.1

EXAMPLE E

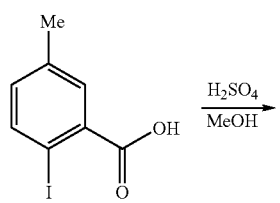

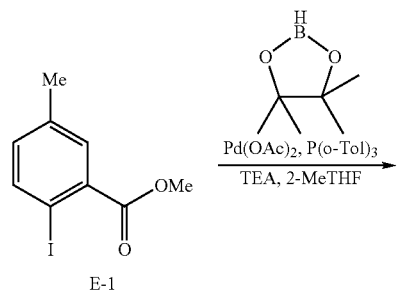

E-1

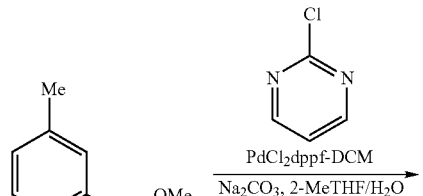

E-2

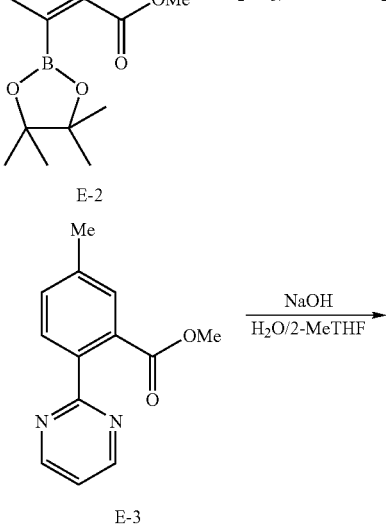

E-3

E-4

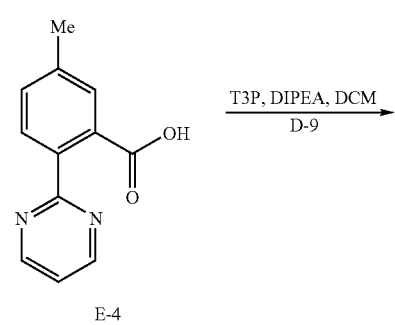

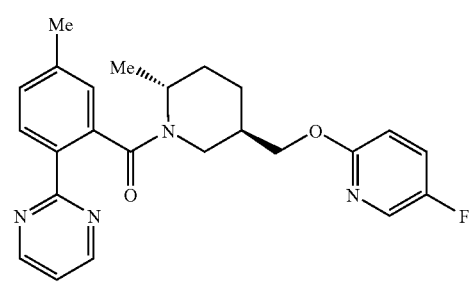

E-5

Methyl 2-iodo-5-methylbenzoate (E-1)

A visually clean 100 L flask equipped with a mechanical stirrer thermocouple and water chilled condenser was charged with MeOH (50 L). 2-iodo-5-methylbenzoic acid (5.85 kg, 22.32 mol) was then added while stirring. Concentrated sulfuric acid (0.595 L, 11.16 mol) was then added portion-wise which caused an increase in temperature from 17° C. to 22° C. This mixture was gradually brought to an internal temperature of 64.6° C. an aged overnight (~18 h). The next morning the reaction had reached >98% conversion by HPLC. The flask was cooled to 16° C. by placing in an ice bath and 850 ml of 10N NaOH (0.98 equiv.) was added slowly (over 10 minutes) while monitoring the pH. After the addition the pH was 5-6 (Caution: bringing pH over 9 can result in saponification during the work-up). The solution was then concentrated to about 16 L and this suspension was transferred to a 100 L extractor. The flask was rinsed with 8 L of IPAc and 4 L of water which were also transferred to the extractor. 32 L IPAc along with 10 L of 5w % $NaHCO_3$ and ~10 L of 15w % Brine. The layers were cut and the aqueous layers were back-extracted with 20 L of IPAc. The organic layers were then combined and washed with 10 L of 15w % Brine. The organic layers were collected to provide E-1 (6.055 kg, 21.93 mol, 98% yield) in 98.3% purity.

Methyl 5-methyl-2-(4,4,5,5-tetramethyl-1,3,2-dioxaborolan-2-yl)benzoate (E-2)

A solution of E-1 (5.9 kg, 21.37 mol) in iPAc was charged in a visually clean 100 L equipped with a mechanical stirrer and thermocouple. The solution was solvent switched to 2-MeTHF (~35 L). Triethylamine (8.94 L, 64.1 mol) was added and the solution was degassed with $N_2$. Pinacol borane (4.65 L, 32.1 mol) was added slowly (over 15 minutes) to the stirring solution while maintaining the purge. The solution was further degassed for 10 minutes and tri-o-tolylphosphine (0.325 kg, 1.069 mol) was added followed by palladium (II) acetate (0.120 kg, 0.534 mol). This caused the reaction to turn black immediately with a slow exotherm from 11.5° C. to 30° C. At this point a delayed exotherm was observed and the reaction temperature increased to 60° C. (over 45 minutes). The reaction temperature was increased to 77° C. and aged for another 45 minutes. At this point, HPLC analysis of a reaction aliquot revealed complete consumption of the starting material. The heat source was removed and an ice bath was placed under the flask to cool the reaction over 1.5 hours. A 26w % ammonium chloride solution is added very slowly to control gas evolution and exotherm (over 60 minutes) which caused a black precipitated to form. The supernatant was transferred to the extractor which already contained 40 L of water. The black slurry remaining was filtered on Solka Floc and washed with MTBE (~20 L). The filtrate was loaded into the extractor. The layers were cut and assay of the organic layers revealed E-2 (4.45 kg, 16.11 mol, 75% yield) in 81.6% purity and was used as is in the following step.

Methyl 5-methyl-2-pyrimidin-2-ylbenzoate (E-3)

A solution of E-2 (4.38 kg, 15.84 mol) from the previous reaction was charged in a visually clean 100 L reactor equipped with a mechanical stirrer and a thermocouple. The mixture was solvent switched to 2-MeTHF (35 L). This was followed by addition of 2-chloropyrimidine (2.18 kg, 19.01 mol) (endothermic 19 to 14° C.) and sodium carbonate (5.04 kg, 47.5 mol). To this stirring suspension was added water (11.67 L) (exothermic 15-24° C.). The thick slurry was degassed with $N_2$ for 40 minutes after which $PdCl_2(dppf)$-$CH_2Cl_2$ adduct (0.518 kg, 0.634 mol) was added which causes the reaction to become black. The internal temperature was set to 74° C. and aged for 16 h. An aliquot was taken for HPLC analysis and revealed near complete consumption of the starting boronate (>97% conv.). The reaction was cooled to room temperature, and 12 L of water and 24 L of MTBE were added while maintaining stirring for 10 minutes. This solution was filtered on Solka floc and transferred to a 100 L extractor. The flask was further rinsed with 4 L of both MTBE and water (x2) and then another 4 L of MTBE. The layers were cut and the aqueous layers were back-extracted with 21.5 L of MTBE. Assay of the organic layers showed the biaryl ester (2.76 kg, 12.09 mol, 76% yield). The organics were reloaded into the extractor and 1.26 kg of Darco KB-G was added and the mixture was stirred for 2 hours and then filtered over Solka floc. The filter cake was washed with 3×10 L of MTBE. Heavy metal analysis revealed 427-493 ppm of Pd and 882-934 ppm of Fe. Assay was 2.381 kg of E-3 (66% overall, 86% recovery from DARCO). Data for E-3: $^1$H NMR (500 MHz, $CDCl_3$, 293K, TMS): 8.78 (d, J=4.87 Hz, 2 H); 7.97 (d, J=7.93 Hz, 1 H); 7.51 (s, 1 H); 7.39 (d, J=7.99 Hz, 1 H); 7.19 (t, J=4.88 Hz, 1 H); 3.75 (s, 3 H); 2.44 (s, 3 H).

5-Methyl-2-pyrimidin-2-ylbenzoic acid (E-4)

A solution of E-3 from the previous step was charged to a visually clean 100 L flask through an in-line filter, concentrated and solvent switched to 2-MeTHF (~15 L). To this solution was added water (20 L) and then sodium hydroxide (10N) (2.60 L, 26.0 mol). After the addition the reaction turned red and the heat source was set to 72° C. The mixture was aged at this temperature for 1.5 hours after which complete conversion was observed by HPLC analysis. The reaction was cooled and transferred to a 50 L extractor. The flask was rinsed with 4 L of water and 10 L of MTBE which was added to the stirring mixture in the extractor. The layers were cut, and the aqueous phase was washed twice with 10 L of MTBE. The aqueous layer was then re-introduced into the reactor (100 L) through an in-line filter for the acidification. 2.3 L of 12 N HCl was added slowly to the cold mixture which causes an exotherm from 7 to 10° C. This caused a beige precipitate to form (pH=1). This precipitate was filtered. The beige filter cake was washed twice with 3 mL/g of cold water. Then the cake was washed with 3 mL/g of cold 15% MTBE/Heptane and 15% PhMe/Heptane. Finally it was washed with 1.5 mL/g of room temperature MTBE and twice with room temperature 3 mL/g Heptane. The solid was then dried under a stream of $N_2$ for 2 days to provide E-4 as a light beige powder (2.15 kg, 10.04 mol, 97% yield). HPLC analysis reveals the product to be 99.2% purity. Heavy metal analysis revealed 264 ppm of Pd and 19.7 ppm of Fe. Data for E-4: $^1$H NMR (500 MHz, DMSO-$d_6$): 12.65 (s, 1 H); 8.85-8.82 (m, 2 H); 7.78 (dd, J=7.89, 2.34 Hz, 1 H); 7.49-7.37 (m, 3 H); 2.40 (s, 3 H).

2-{2-[((2R,5R)-5-{[(5-Fluoropyridin-2-yl)oxy]methyl}-2-methylpiperidin-1-yl)carbonyl]-4-methylphenyl}pyrimidine (E-5)

The solution of D-9 (1 kg, 4.46 mol) was charged in a visually clean and dry 50 L flask equipped with a thermocouple and mechanical stirrer and was solvent switched to DCM (11.00 L). DIPEA (2 L, 11.45 mol) is added and then E-4 (1.22 kg, 5.67 mol) was added to this stirring solution. This solution was cooled with an ice bath (12 C). To this stirring solution was added T3P (7.87 L, 13.38 mol) through an addition funnel keeping the reaction temperature <21° C. over 1 h. Once addition was completed, the reaction became yellow and heterogenous. To facilitate stirring 2 L of DCM were added. The reaction was heated to 44° C. (small exotherm at 42° C., which causes the temperature to rise to 46.7° C. and maintain that temperature for 30 min). The reaction was aged at this temperature overnight. After 17 h the reaction was not complete and T3P (1.1 L, 1.870 mol) was added to accelerate conversion. The next day (42 h) the reaction was deemed complete by HPLC and was cooled in an ice bath to 4° C. 20 L of water was added (slowly for the first 1.5 L then pretty fast.) keeping the reaction temperature under 17° C. This mixture was stirred at room temperature for 30 minutes. Then the mixture was transferred into a 50 L extractor charged with 20 L of MTBE. The flask was rinsed with an additional 2 L of water and 4 L of MTBE. The layers were cut and the organics are washed with 20 L 1N NaOH and then 10 L of 1N NaOH. Finally, the organics were washed twice with 10 L of brine 15%. The organic fractions (quantitative HPLC assay at 1.65 kg) are then treated with ~50w % of Darco KB (750 g) for 1.75 h, filtered on Solka floc and rinsed with 10 mL/g of MTBE (1.559 kg, 94.5% recovery). To a visually clean and dry 50 L RBF equipped with a mechanical stirrer, a thermocouple, a reflux condenser and a nitrogen inlet was charged the crude material from above (E-5 solution and all solvents used were filtered using a 1 µm in-line filter). The reaction mixture was solvent switched to IPAc and the final volume was adjusted to 7.5 L (about 4 mL/g of IPAc). The reaction mixture was warmed to 75° C. (all soluble), cooled to room temperature slowly and seeded at 45° C. with 18 g of E-5 (front run material, obtained from rex in IPAc/heptane) stirred overnight (16 hr) at room temperature then heptane was added (6 ml/g) over 60 min. The reaction mixture was aged for 1 hr before to be cooled to 5° C. and stirred for 30 min. The suspension was then transferred onto a filter pot and rinsed with IPAC/heptane (2×3 mL/g of cold 15% IPAc) and heptane (5 mL/g). The residual beige solid was dried under a flow of nitrogen for 18 hr (the product was found to be dry with <0.3 wt % of solvents). 1.2 kg of E-5 was isolated as a light beige solid (99.4 LCAP, >99.5 ee, >99.5% dr, Pd level of 8 ppm and KF of 0.1). Data for E-5: HRMS m/z (M+H): 421.2067, found. 421.2035, required.

EXAMPLE F

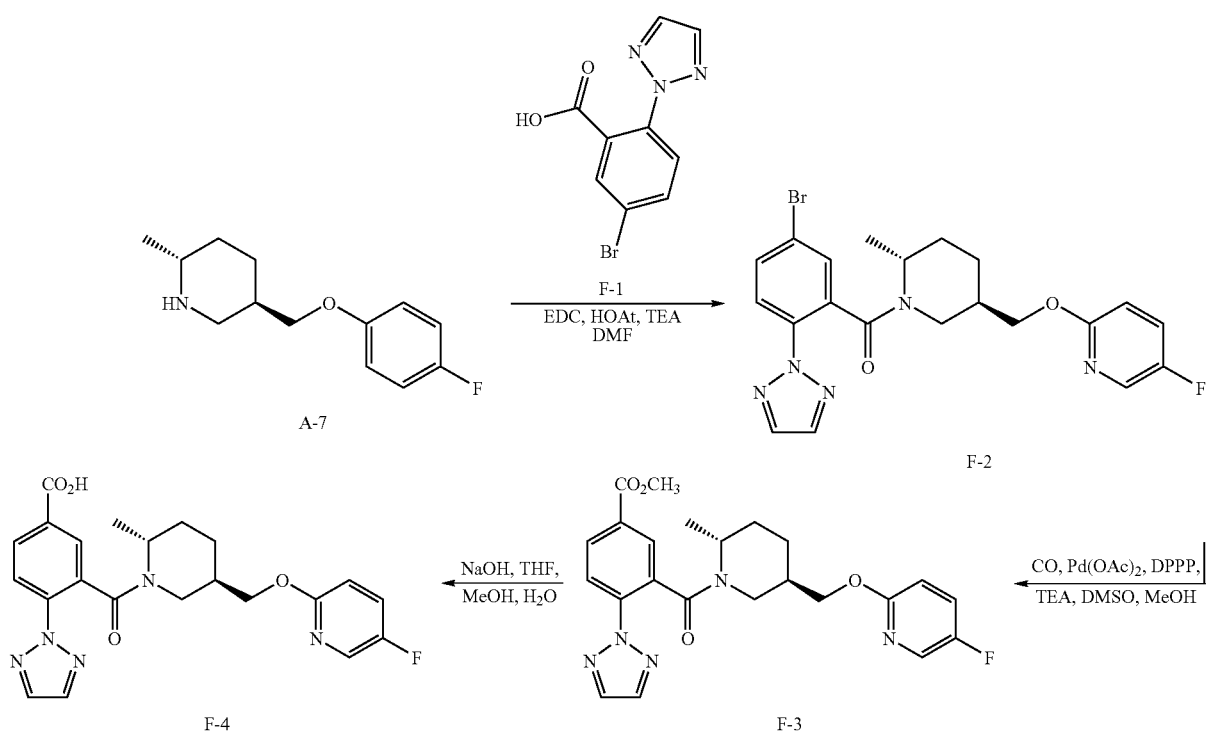

2-({(3R,6R)-1-[5-Bromo-2-(2H-1,2,3-triazol-2-yl) benzoyl]-6-methylpiperidin-3-yl}methoxy)-5-fluoropyridine (F-2)

To a solution of 250 mg (1.12 mmol) of A-7, 299 mg (1.12 mmol) F-1 (prepared in an analogous manner as A-8 starting from 5-bromo-2-iodobenzoic acid), 182 mg (1.34 mmol) 1-hydroxy-7-azabenzotriazole, and 0.47 mL (3.34 mmol) triethylamine in 3 mL of DMF was added 321 mg (1.67 mmol) EDC and the reaction was stirred for 4 h at 50° C. The reaction was partitioned between EtOAc and saturated aqueous NaHCO₃, washed with water, brine, dried over MgSO₄, and concentrated by rotary evaporation to provide F-2 as a gum. Data for F-2: LC/MS: rt=2.64 min; m/z (M+H)=474.1 found; 474.1 required.

Methyl 3-[((2R,5R)-5-{[(5-fluoropyridin-2-yl)oxy] methyl}-2-methylpiperidin-1-yl)carbonyl]-4-(2H-1, 2,3-triazol-2-yl)benzoate (F-3)

Carbon monoxide was bubbled through a solution of 529 mg (1.12 mmol) of F-2, mg (0.11 mmol) palladium(II) acetate, 46 mg (0.11 mmol) 1,3-bis(diphenylphosphino)-propane, and 0.62 mL (4.5 mmol) triethylamine in 15 mL of methanol and 7.5 ml of DMSO at 80° C. for 10 minutes. The reaction was then placed under a balloon of carbon monoxide and stirred at 80° C. overnight. The reaction was partitioned between EtOAc and saturated aqueous NaHCO₃, washed with water, brine, dried over MgSO₄, and concentrated by rotary evaporation. The residue was purified by column chromatography on silica gel (EtOAc/hexanes) to provide F-3 as an off-white solid. Data for F-3: LC/MS: rt=2.30; m/z (M+H) =454.1 found; 454.2 required.

3-[((2R,5R)-5-{[(5-Fluoropyridin-2-yl)oxy]methyl}-2-methylpiperidin-1-yl)carbonyl]-4-(2H-1,2,3-triazol-2-yl)benzoic acid (F-4)

To 95 mg (0.21 mmol) F-3 in 15 mL of 1:1:1 MeOH/THF/H₂O was added 0.84 mL (0.84 mmol) 1M aqueous sodium hydroxide solution and the mixture was stirred for three hours at 50° C. The reaction was filtered, concentrated to remove organic solvents, diluted with EtOAc and washed with 1M NaOH three times. Aqueous layers were acidified with 1M HCl, washed three times with DCM and dried over MgSO₄. Following concentration by rotary evaporation, the residue was suspended in Et₂O/hexanes and concentrated to provide F-4 as a white solid. Data for F-4: LC/MS: rt=2.02 min; m/z (M+H)=440.2 found; 440.2 required. HRMS (ESI) m/z (M+H): 440.1744, found; 440.1729, required.

EXAMPLE G

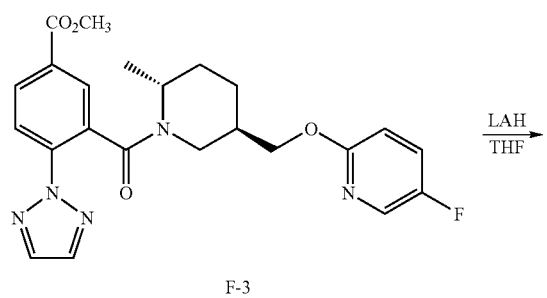

LAH
THF

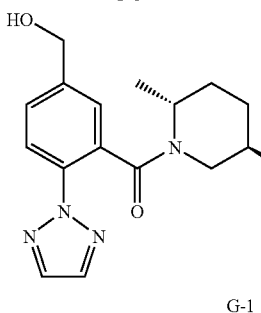

G-1

[3-[((2R,5R)-5-{[(5-Fluoropyridin-2-yl)oxy]methyl}-2-methylpiperidin-1-yl)carbonyl]-4-(2H-1,2,3-triazol-2-yl)phenyl]methanol (G-1)

To 175 mg (0.39 mmol) F-3 in 20 mL of THF at 0° C. was added 1.89 mL (3.78 mmol) 2M lithium aluminum hydride solution in THF and the mixture was stirred for 3.5 hours while allowing to warm to room temperature. The reaction was quenched with 0.15 ml water, 0.15 ml 15% aqueous NaOH solution and 0.45 ml water and then filtered through a pad of Celite. Following concentration by rotary evaporation, the residue was purified by flash column chromatography (hexanes/EtOAc), concentrated, suspended in Et₂O/hexanes and concentrated again to provide G-1 as a white solid. Data for G-1: LC/MS: rt=2.00 min; m/z (M+H)=426.2 found; 426.2 required. HRMS (ESI) m/z (M+H) 426.1943 found; 426.1936 required.

EXAMPLE H

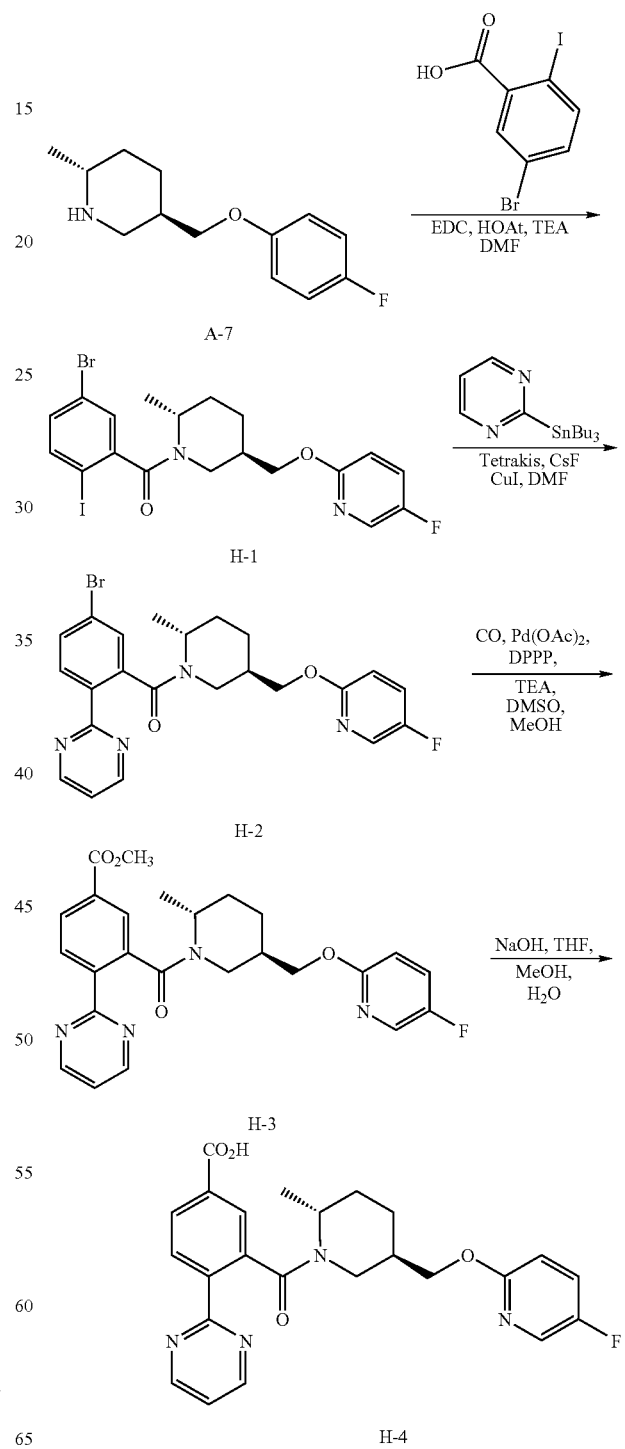

2-{[(3R,6R)-1-(5-Bromo-2-iodobenzoyl)-6-methylpiperidin-3-yl]methoxy}-5-fluoropyridine (H-1)

To a solution of 350 mg (1.56 mmol) of A-7, 510 mg (1.56 mmol) 5-bromo-2-iodobenzoic acid, 255 mg (1.87 mmol) 1-hydroxy-7-azabenzotriazole, and 0.65 mL (4.68 mmol) triethylamine in 5 mL of DMF was added 449 mg (2.34 mmol) EDC and the reaction was stirred for four hours at 50° C. The reaction was partitioned between EtOAc and saturated aqueous NaHCO$_3$, washed with water, brine, dried over MgSO$_4$, and concentrated by rotary evaporation to provide H-1 as a gum. Data for H-1: LC/MS: rt=2.81 min; m/z (M+H)=533.0 found; 533.0 required.

2-{4-Bromo-2-[((2R,5R)-5-{[(5-fluoropyridin-2-yl)oxy]methyl}-2-methylpiperidin-1-yl)carbonyl]phenyl}pyrimidine (H-2)

To a suspension of 230 mg (0.43 mmol) of H-1, 207 mg (0.56 mmol) 2-tributylstannylpyrimidine, 131 mg (0.86 mmol) CsF and 8 mg (0.04 mmol) CuI in 3 mL of DMF was added 50 mg (0.04 mmol) tetrakistriphenylphosphinepalladium(0) and the reaction was heated in a microwave for 10 minutes at 130° C. The reaction was partitioned between EtOAc and saturated aqueous NaHCO$_3$, washed with water, brine, dried over MgSO$_4$, and concentrated by rotary evaporation. The residue was purified by column chromatography on silica gel (EtOAc/hexanes) to provide H-2 as a yellow gum. Data for H-2: LC/MS: rt=2.61 min; m/z (M+H)=485.1 found; 485.1 required.

Methyl 3-[((2R,5R)-5-{[(5-fluoropyridin-2-yl)oxy]methyl}-2-methylpiperidin-1-yl)carbonyl]-4-pyrimidin-2-ylbenzoate (H-3)

Carbon monoxide was bubbled through a solution of 500 mg (1.03 mmol) of H-2, 23.1 mg (0.10 mmol) palladium(II) acetate, 43 mg (0.10 mmol) 1,3-bis(diphenylphosphino)-propane, and 0.57 mL (4.1 mmol) triethylamine in 15 mL of methanol and 7.5 ml of DMSO at 80° C. for 10 minutes. The reaction was then placed under a balloon of carbon monoxide and stirred at 80° C. for 2.5 hours. The reaction was partitioned between EtOAc and saturated aqueous NaHCO$_3$, washed with water, brine, dried over MgSO$_4$, and concentrated by rotary evaporation. The residue was purified by column chromatography on silica gel (EtOAc/hexanes) to provide H-3 as an off-white solid. Data for H-3: LC/MS: rt=2.30; m/z (M+H)=465.2 found; 465.2 required. HRMS (ESI) m/z (M+H) 465.1944 found; 465.1933 required.

3-[((2R,5R)-5-{[(5-fluoropyridin-2-yl)oxy]methyl}-2-methylpiperidin-1-yl)carbonyl]-4-pyrimidin-2-ylbenzoic acid (H-4)

To 150 mg (0.32 mmol) H-3 in 5 mL each of MeOH/THF/H$_2$O was added 0.97 mL (0.97 mmol) 1M aqueous sodium hydroxide solution and the mixture was stirred for 30 min. at 50° C. The reaction was neutralized to pH=7 with 1M HCl and washed three times with EtOAc. The organic layers were washed with brine, dried over MgSO$_4$ and concentrated by rotary evaporation to provide H-4 as an off-white solid. Data for H-4: LC/MS: rt=1.91 min; m/z (M+H)=451.2 found; 451.2 required. HRMS (ESI) m/z (M+H) 451.1761 found; 451.1776 required.

EXAMPLE I

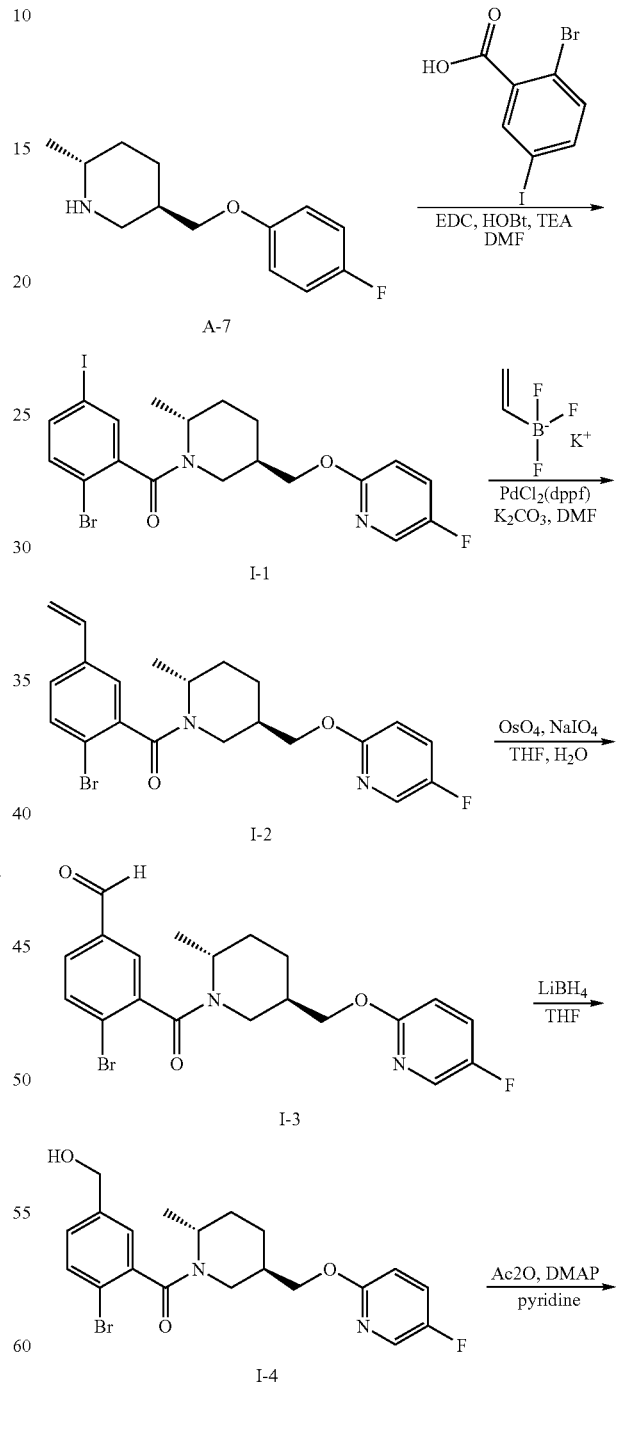

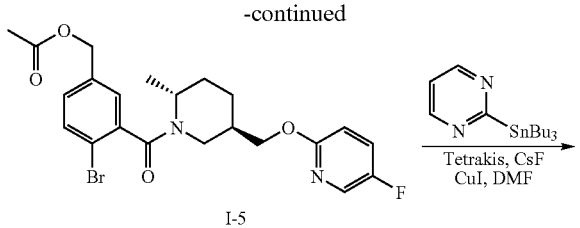

I-5

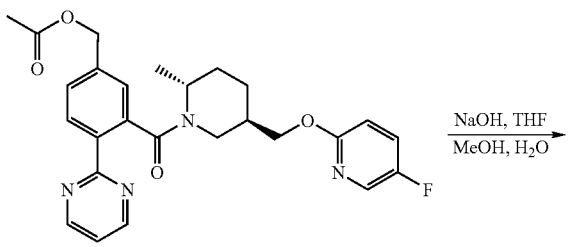

I-6

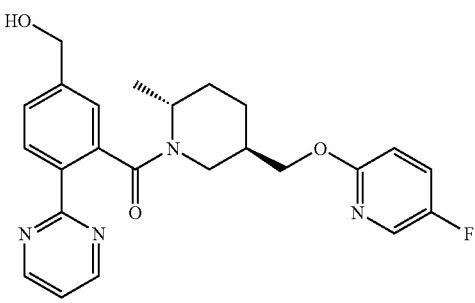

I-7

2-{[(3R,6R)-1-(2-Bromo-5-iodobenzoyl)-6-methylpiperidin-3-yl]methoxy}-5-fluoropyridine To a solution of 3 g (13.4 mmol) of A-7, 4.59 g (14.1 mmol) 2-bromo-5-iodobenzoic acid, 2.46 g (16.1 mmol) 1-hydroxybenzotriazole monohydrate, and 5.6 mL (40.1 mmol) triethylamine in 60 mL of DMF was added 3.85 g (20.1 mmol) EDC and the reaction was stirred for eighteen hours at room temperature. The reaction was partitioned between EtOAc and saturated aqueous NaHCO$_3$, washed with water, brine, dried over MgSO$_4$, and concentrated by rotary evaporation. The residue was purified by column chromatography on silica gel (EtOAc/hexanes) to provide I-1 as a gum. Data for I-1: LC/MS: rt=2.75 min; m/z (M+H)=532.9 found; 533.0 required.

2-{[(3R,6R)-1-(2-Bromo-5-vinylbenzoyl)-6-methylpiperidin-3-yl]methoxy}-5-fluoropyridine (I-2)

To a suspension of 6.85 g (12.9 mmol) of I-1, 2.24 g (16.7 mmol) potassium vinyltrifluoroborate, and 5.33 g (38.5 mmol) K$_2$CO$_3$ in 35 mL of DMF was added 940 mg (1.3 mmol) PdCl$_2$(dppf) and the reaction was purged with argon for 5 minutes then heated at 85° C. for four hours. The reaction was stirred at room temperature for 3 days then partitioned between EtOAc and saturated aqueous NaHCO$_3$, washed with water, brine, dried over MgSO$_4$, and concentrated by rotary evaporation. The residue was purified by column chromatography on silica gel (EtOAc/hexanes) to provide I-2 as a gum. Data for I-2: LC/MS: rt=2.80 min; m/z (M+H)=433.0 found; 433.1 required.

4-Bromo-3-[((2R,5R)-5-{[(5-fluoropyridin-2-yl)oxy]methyl}-2-methylpiperidin-1-yl)carbonyl]benzaldehyde (I-3)

To a solution of 4.2 g (9.7 mmol) of I-2 and 5.7 g (26.6 mmol) sodium periodate in 50 mL of THF and 20 ml water was added 1.42 ml (0.11 mmol) of a 2.5% wt. % solution of osmium tetraoxide solution in tert-butanol and the reaction was stirred at room temperature for four hours. The reaction was partitioned between EtOAc and saturated aqueous NaHCO$_3$, washed with water, brine, dried over MgSO$_4$, and concentrated by rotary evaporation to provide I-3 as a gum. Data for I-3: LC/MS: rt=2.38 min; m/z (M+H)=435.0 found; 435.1 required.

{4-Bromo-3-[((2R,5R)-5-{[(5-fluoropyridin-2-yl)oxy]methyl}-2-methylpiperidin-1-yl)carbonyl]phenyl}methanol (I-4)

To a solution of 3.94 g (9.1 mmol) of I-3 in 50 mL of THF was added 5.4 ml (10.9 mmol) of a 2 M solution of lithium borohydride in THF and the reaction was stirred at room temperature for thirty minutes. The reaction was quenched with saturated aqueous NH$_4$Cl solution and partitioned between EtOAc and saturated aqueous NaHCO$_3$, washed with water, brine, dried over MgSO$_4$, and concentrated by rotary evaporation to provide I-4 as a gum. Data for I-4: LC/MS: rt=2.16 min; m/z (M+H)=437.0 found; 437.1 required.

4-Bromo-3-[((2R,5R)-5-{[(5-fluoropyridin-2-yl)oxy]methyl}-2-methylpiperidin-1-yl)carbonyl]benzyl acetate (I-5)

To a solution of 3.87 g (8.9 mmol) of I-4, 22 mg (0.18 mmol) of DMAP in 50 mL of pyridine was added 1.67 ml (17.7 mmol) of acetic anhydride and the reaction was stirred at room temperature for thirty minutes. The reaction was partitioned between EtOAc and saturated aqueous NaHCO$_3$, washed with water, brine, dried over MgSO$_4$, and concentrated by rotary evaporation. The residue was purified by column chromatography on silica gel (EtOAc/hexanes) to provide I-5 as a gum. Data for I-5: LC/MS: rt=2.55 min; m/z (M+H)=479.0 found; 479.1 required.

3-[((2R,5R)-5-{[(5-Fluoropyridin-2-yl)oxy]methyl}-2-methylpiperidin-1-yl)carbonyl]-4-pyrimidin-2-ylbenzyl acetate (I-6)

To a suspension of 134 mg (0.28 mmol) of I-5, 310 mg (0.84 mmol) 2-tributylstannylpyrimidine, 170 mg (1.12 mmol) CsF and 16 mg (0.08 mmol) CuI in 3 mL of DMF was added 32 mg (0.03 mmol) tetrakistriphenylphenylphosphinepalladium(0) and the reaction was heated in a microwave at 150° C. for 25 minutes. The reaction was partitioned between EtOAc and saturated aqueous NaHCO$_3$, washed with water, brine, dried over MgSO$_4$, and concentrated by rotary evaporation. The residue was purified by column chromatography on silica gel (EtOAc/hexanes) to provide I-6 as a gum. Data for I-6: LC/MS: rt=2.26 min; m/z (M+H)=479.1 found; 479.2 required.

{3-[((2R,5R)-5-{[(5-Fluoropyridin-2-yl)oxy]methyl}-2-methylpiperidin-1-yl)carbonyl]-4-pyrimidin-2-ylphenyl}methanol (I-7)

To 830 mg (1.74 mmol) I-6 in 5 mL each of MeOH/THF/H$_2$O was added 5.2 mL (5.2 mmol) 1M aqueous sodium hydroxide solution and the mixture was stirred for three hours at room temperature. The reaction was concentrated to remove organic solvents and then partitioned between EtOAc and saturated aqueous NaHCO$_3$, washed with water, brine, dried over MgSO$_4$, and concentrated by rotary evaporation. The residue was purified by column chromatography on silica gel (CHCl$_3$:EtOAc:MeOH/CHCl$_3$) and following concentration by rotary evaporation, the residue was suspended in Et$_2$O/hexanes and concentrated to provide I-7 as a white solid. Data for I-7: LC/MS: rt=1.97 min; m/z (M+H)=437.1 found; 437.2 required. HRMS (ESI) m/z (M+H) 437.1966 found; 437.1983 required.

The following compounds were prepared using the foregoing methodology, but substituting the appropriately substituted reagent, as described in the foregoing Reaction Schemes and Examples. The requisite starting materials were commercially available, described in the literature or readily synthesized by one skilled in the art of organic synthesis without undue experimentation. Some final products were purified by flash chromatography (SiO$_2$; EtOAc/hexanes or other appropriate solvent system) and were isolated as the free-base; alternately, some products were purified by reverse phase HPLC (CH$_3$CN/H$_2$O containing 0.1% TFA as a modifier) and isolated as the TFA salt, in which case the masses reported and found are for the free-base. Alternatively, fractions containing the product could be basified with NaHCO$_3$ and extracted with EtOAc, dried over Na$_2$SO$_4$, and concentrated to provide the free-base.

| Cpd | Structure | Name | HRMS m/z (M + H) |
|---|---|---|---|
| 1-1 | 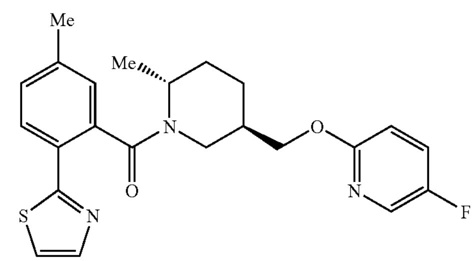 | 5-fluoro-2-({(3R,6R)-6-methyl-1-[5-methyl-2-(1,3-thiazol-2-yl)benzoyl]piperidin-3-yl}methoxy)pyridine | 426.166 found, 426.1646 required. |
| 1-2 | 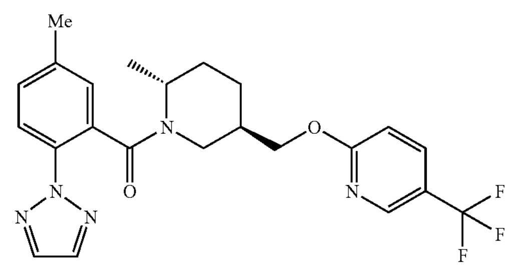 | 2-({(3R,6R)-6-methyl-1-[5-methyl-2-(2H-1,2,3-triazol-2-yl)benzoyl]piperidin-3-yl}methoxy)-5-(trifluoromethyl)pyridine | 460.1955 found, 460.1955 required. |
| 1-3 | 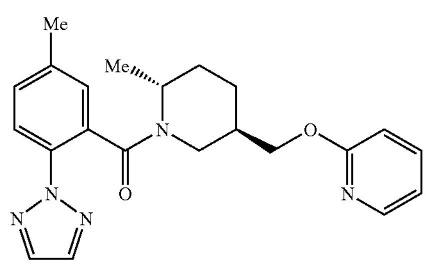 | 2-({(3R,6R)-6-methyl-1-[5-methyl-2-(2H-1,2,3-triazol-2-yl)benzoyl]piperidin-3-yl}methoxy)pyridine | 392.2095 found, 392.2081 required. |
| 1-4 | 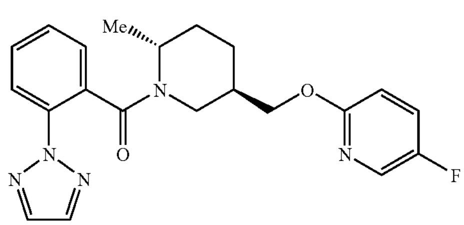 | 5-fluoro-2-({(3R,6R)-6-methyl-1-[2-(2H-1,2,3-triazol-2-yl)benzoyl]piperidin-3-yl}methoxy)pyridine | 396.1831 found, 396.1831 required. |

-continued

| Cpd | Structure | Name | HRMS m/z (M + H) |
|---|---|---|---|
| 1-5 | 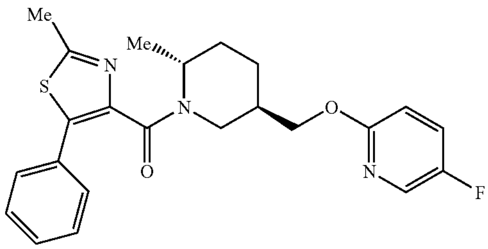 | 5-fluoro-2-({(3R,6R)-6-methyl-1-[(2-methyl-5-phenyl-1,3-thiazol-4-yl)carbonyl]piperidin-3-yl}methoxy)pyridine | 426.164 found, 426.1646 required. |
| 1-6 | 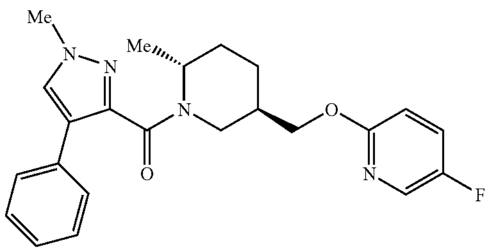 | 5-fluoro-2-({(3R,6R)-6-methyl-1-[(1-methyl-4-phenyl-1H-pyrazol-3-yl)carbonyl]piperidin-3-yl}methoxy)pyridine | 409.2051 found, 409.2035 required. |
| 1-7 | 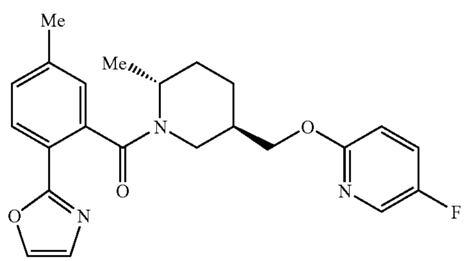 | 5-fluoro-2-({(3R,6R)-6-methyl-1-[5-methyl-2-(1,3-oxazol-2-yl)benzoyl]piperidin-3-yl}methoxy)pyridine | 410.1875 found, 410.1875 required. |
| 1-8 | 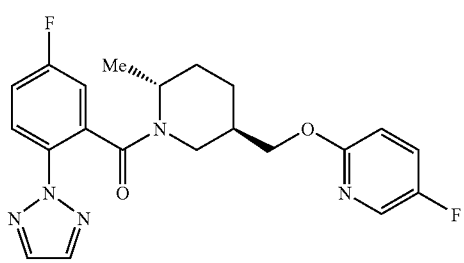 | 5-fluoro-2-({(3R,6R)-1-[5-fluoro-2-(2H-1,2,3-triazol-2-yl)benzoyl]-6-methylpiperidin-3-yl}methoxy)pyridine | 414.1747 found, 414.1736 required. |
| 1-9 | 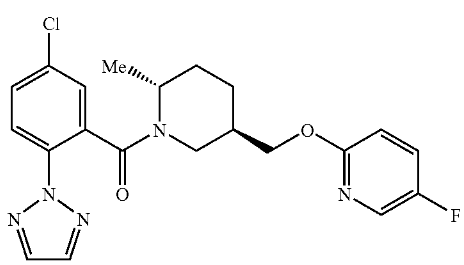 | 2-({(3R,6R)-1-[5-chloro-2-(2H-1,2,3-triazol-2-yl)benzoyl]-6-methylpiperidin-3-yl}methoxy)-5-fluoropyridine | 430.1442 found, 430.1441 required. |
| 1-10 | 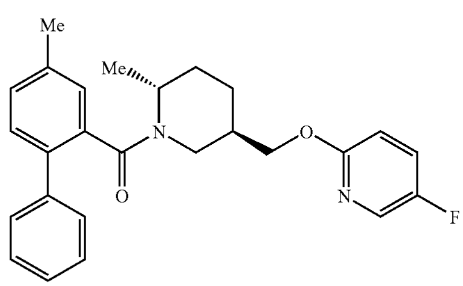 | 5-fluoro-2-({(3R,6R)-6-methyl-1-[(4-methylbiphenyl-2-yl)carbonyl]piperidin-3-yl}methoxy)pyridine | 419.2127 found, 419.2129 required. |

-continued

| Cpd | Structure | Name | HRMS m/z (M + H) |
|---|---|---|---|
| 1-11 | 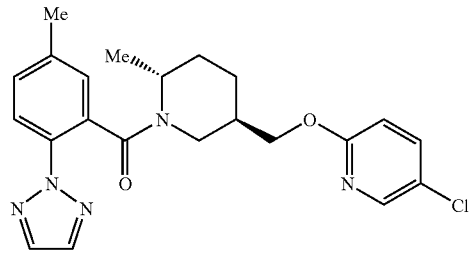 | 5-chloro-2-({(3R,6R)-6-methyl-1-[5-methyl-2-(2H-1,2,3-triazol-2-yl)benzoyl]piperidin-3-yl}methoxy)pyridine | 426.1702 found, 426.1691 required. |
| 1-12 | 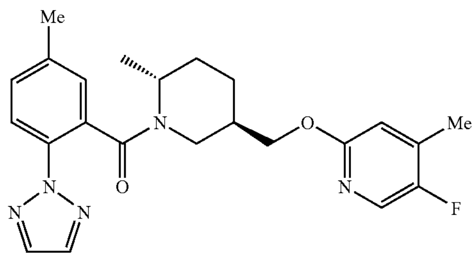 | 5-fluoro-4-methyl-2-({(3R,6R)-6-methyl-1-[5-methyl-2-(2H-1,2,3-triazol-2-yl)benzoyl]piperidin-3-yl}methoxy)pyridine | 424.2145 found, 424.2143 required. |
| 1-13 | 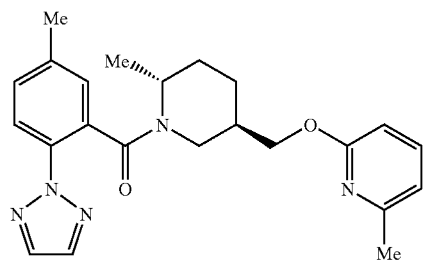 | 2-methyl-6-({(3R,6R)-6-methyl-1-[5-methyl-2-(2H-1,2,3-triazol-2-yl)benzoyl]piperidin-3-yl}methoxy)pyridine | 406.2241 found, 406.2238 required. |
| 1-14 | 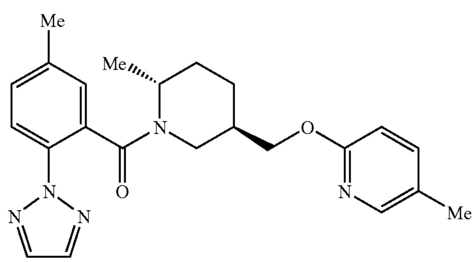 | 5-methyl-2-({(3R,6R)-6-methyl-1-[5-methyl-2-(2H-1,2,3-triazol-2-yl)benzoyl]piperidin-3-yl}methoxy)pyridine | 406.2241 found, 406.2238 required. |
| 1-15 | 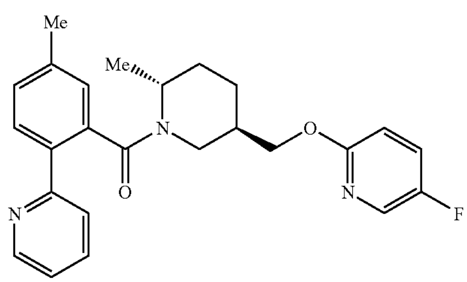 | 5-fluoro-2-{[(3R,6R)-6-methyl-1-(5-methyl-2-pyridin-2-ylbenzoyl)piperidin-3-yl]methoxy}pyridine | 420.2082 found, 420.2082 required. |
| 1-16 | 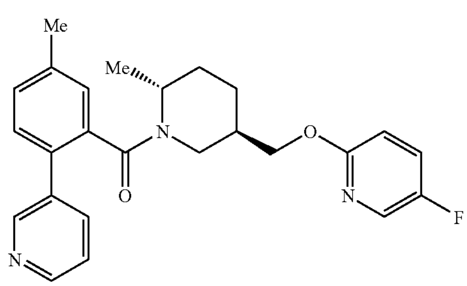 | 5-fluoro-2-{[(3R,6R)-6-methyl-1-(5-methyl-2-pyridin-3-ylbenzoyl)piperidin-3-yl]methoxy}pyridine | 442.1875 found, 442.1901 required. (M + Na) |

-continued

| Cpd | Structure | Name | HRMS m/z (M + H) |
|---|---|---|---|
| 1-17 | 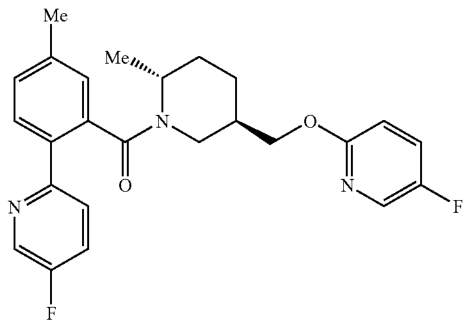 | 5-fluoro-2-({(3R,6R)-1-[2-(5-fluoropyridin-2-yl)-5-methylbenzoyl]-6-methylpiperidin-3-yl}methoxy)pyridine | 438.1966 found, 438.1988 required. |
| 1-18 | 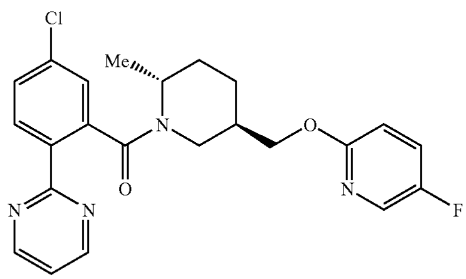 | 2-{4-chloro-2-[((2R,5R)-5-{[(5-fluoropyridin-2-yl)oxy]methyl}-2-methylpiperidin-1-yl)carbonyl]phenyl}pyrimidine | 441.1496 found, 441.1488 required. |
| 1-19 | 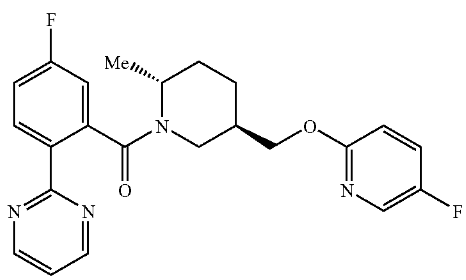 | 2-{4-fluoro-2-[((2R,5R)-5-{[(5-fluoropyridin-2-yl)oxy]methyl}-2-methylpiperidin-1-yl)carbonyl]phenyl}pyrimidine | 425.1786 found, 425.1784 required. |
| 1-20 | 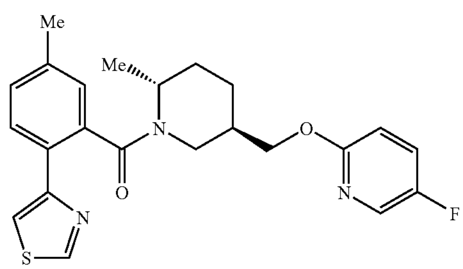 | 5-fluoro-2-({(3R,6R)-6-methyl-1-[5-methyl-2-(1,3-thiazol-4-yl)benzoyl]piperidin-3-yl}methoxy)pyridine | 426.1623 found, 426.1646 required. |
| 1-21 | 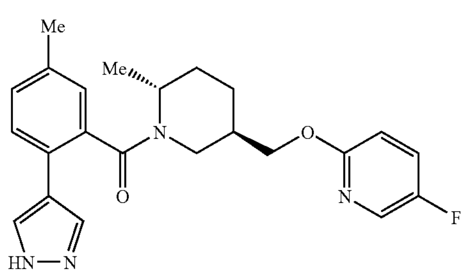 | 5-fluoro-2-({(3R,6R)-6-methyl-1-[5-methyl-2-(1H-pyrazol-4-yl)benzoyl]piperidin-3-yl}methoxy)pyridine | 409.2013 found, 409.2034 required. |

-continued

| Cpd | Structure | Name | HRMS m/z (M + H) |
|---|---|---|---|
| 1-22 | 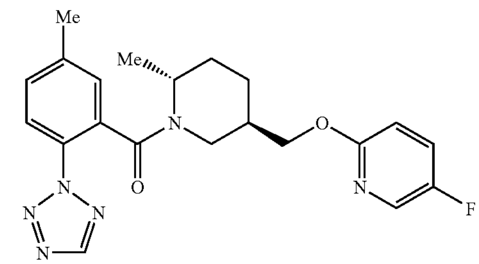 | 5-fluoro-2-({(3R,6R)-6-methyl-1-[5-methyl-2-(2H-tetrazol-2-yl)benzoyl]piperidin-3-yl}methoxy)pyridine | 411.1917 found, 411.1939 required. |
| 1-23 | 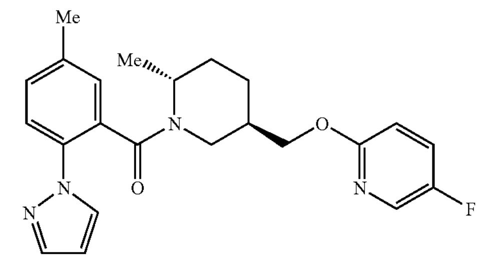 | 5-fluoro-2-({(3R,6R)-6-methyl-1-[5-methyl-2-(1H-pyrazol-1-yl)benzoyl]piperidin-3-yl}methoxy)pyridine | 409.2020 found, 409.2034 required. |
| 1-24 | 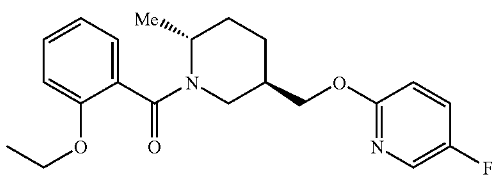 | 2-{[(3R,6R)-1-(2-ethoxybenzoyl)-6-methylpiperidin-3-yl]methoxy}-5-fluoropyridine | 373.1924 found, 373.1922 required. |
| 1-25 | 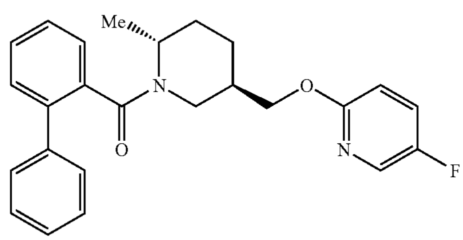 | 2-{[(3R,6R)-1-(biphenyl-2-ylcarbonyl)-6-methylpiperidin-3-yl]methoxy}-5-fluoropyridine | 405.1975 found, 405.1973 required. |
| 1-26 | 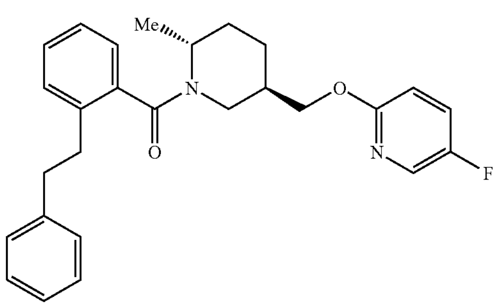 | 5-fluoro-2-({(3R,6R)-6-methyl-1-[2-(2-phenylethyl)benzoyl]piperidin-3-yl}methoxy)pyridine | 433.2287 found, 433.2286 required. |
| 1-27 | 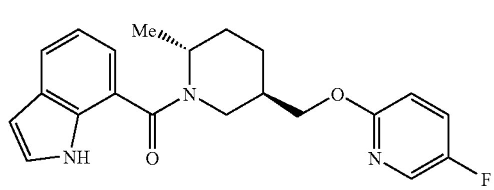 | 7-[((2R,5R)-5-{[(5-fluoropyridin-2-yl)oxy]methyl}-2-methylpiperidin-1-yl)carbonyl]-1H-indole | 368.1780 found, 368.1769 required. |

-continued

| Cpd | Structure | Name | HRMS m/z (M + H) |
|---|---|---|---|
| 1-28 | 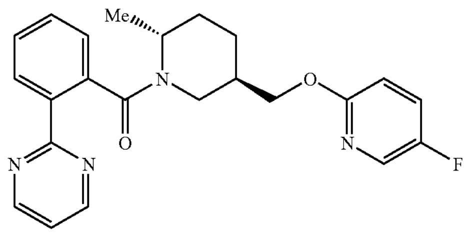 | 2-{2-[((2R,5R)-5-{[(5-fluoropyridin-2-yl)oxy]methyl}-2-methylpiperidin-1-yl)carbonyl]phenyl}pyrimidine | 407.1879 found, 407.1878 required. |
| 1-29 | 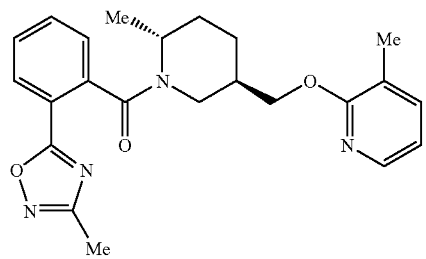 | 3-methyl-2-({(3R,6R)-6-methyl-1-[2-(3-methyl-1,2,4-oxadiazol-5-yl)benzoyl]piperidin-3-yl}methoxy)pyridine | 407.2068 found, 407.2078 required. |
| 1-30 | 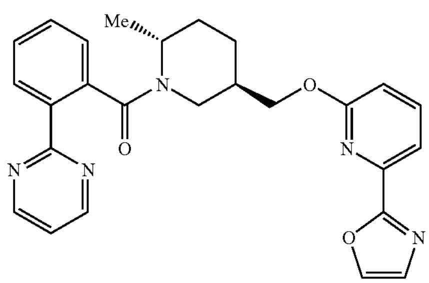 | 2-(2-{[(2R,5R)-2-methyl-5-({[6-(1,3-oxazol-2-yl)pyridin-2-yl]oxy}methyl)piperidin-1-yl]carbonyl}phenyl)pyrimidine | 456.2026 found, 456.2030 required. |
| 1-31 | 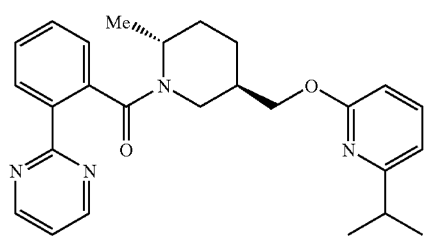 | 2-{2-[((2R,5R)-5-{[(6-isopropylpyridin-2-yl)oxy]methyl}-2-methylpiperidin-1-yl)carbonyl]phenyl}pyrimidine | 431.2435 found, 431.2442 required. |
| 1-32 | 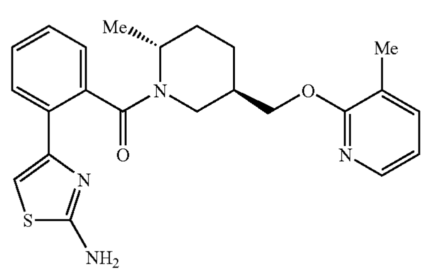 | 4-{2-[((2R,5R)-2-methyl-5-{[(3-methylpyridin-2-yl)oxy]methyl}piperidin-1-yl)carbonyl]phenyl}-1,3-thiazol-2-amine | 423.1842 found, 423.1849 required. |
| 1-33 | 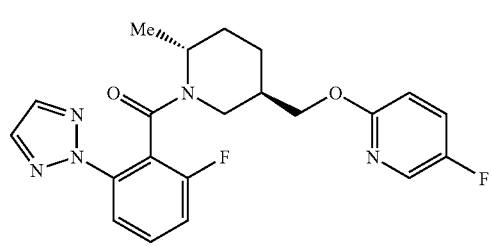 | 5-fluoro-2-({(3R,6R)-1-[2-fluoro-6-(2H-1,2,3-triazol-2-yl)benzoyl]-6-methylpiperidin-3-yl}methoxy)pyridine | 414.1738 found, 414.1736 required. |

-continued

| Cpd | Structure | Name | HRMS m/z (M + H) |
|---|---|---|---|
| 1-34 | 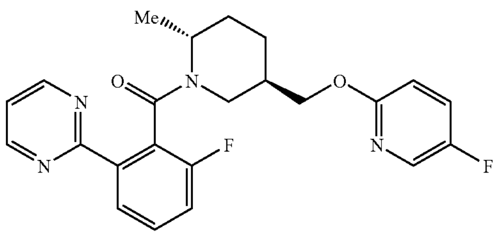 | 2-{3-fluoro-2-[((2R,5R)-5-{[(5-fluoropyridin-2-yl)oxy]methyl}-2-methylpiperidin-1-yl)carbonyl]phenyl}pyrimidine | 425.1786 found, 425.1784 required. |
| 1-35 | 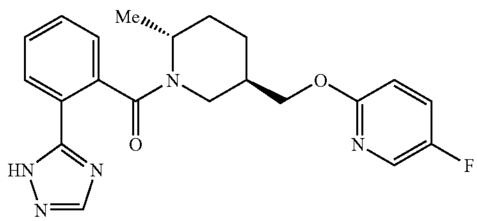 | 5-fluoro-2-({(3R,6R)-6-methyl-1-[2-(1H-1,2,4-triazol-5-yl)benzoyl]piperidin-3-yl}methoxy)pyridine | 396.1833 found, 396.1830 required. |
| 1-36 | 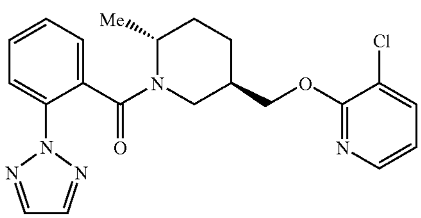 | 3-chloro-2-({(3R,6R)-6-methyl-1-[2-(2H-1,2,3-triazol-2-yl)benzoyl]piperidin-3-yl}methoxy)pyridine | 412.1516 found, 412.1535 required. |
| 1-37 | 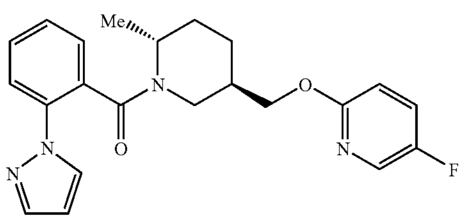 | 5-fluoro-2-({(3R,6R)-6-methyl-1-[2-(1H-pyrazol-1-yl)benzoyl]piperidin-3-yl}methoxy)pyridine | 395.1881 found, 395.1878 required. |
| 1-38 | 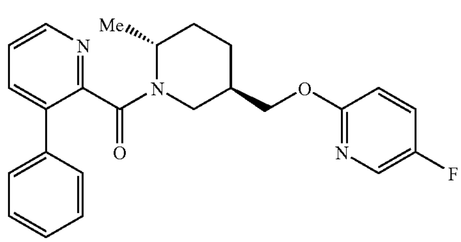 | 2-[((2R,5R)-5-{[(5-fluoropyridin-2-yl)oxy]methyl}-2-methylpiperidin-1-yl)carbonyl]-3-phenylpyridine | 406.1924 found, 406.1925 required. |
| 1-39 | 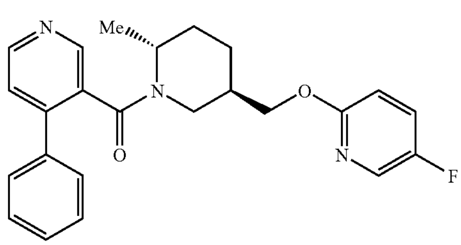 | 5-fluoro-2-({(3R,6R)-6-methyl-1-[(4-phenylpyridin-3-yl)carbonyl]piperidin-3-yl}methoxy)pyridine | 406.1931 found, 406.1925 required. |

-continued

| Cpd | Structure | Name | HRMS m/z (M + H) |
|---|---|---|---|
| 1-40 | 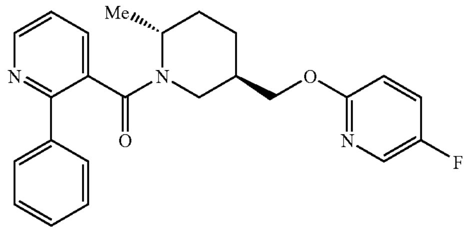 | 3-[((2R,5R)-5-{[(5-fluoropyridin-2-yl)oxy]methyl}-2-methylpiperidin-1-yl)carbonyl]-2-phenylpyridine | 406.1936 found, 406.1925 required. |
| 1-41 | 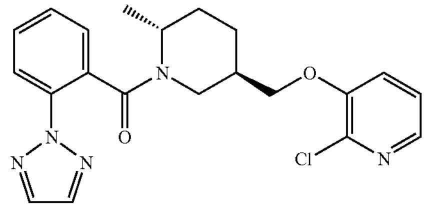 | 2-chloro-3-({(3R,6R)-6-methyl-1-[2-(2H-1,2,3-triazol-2-yl)benzoyl]piperidin-3-yl}methoxy)pyridine | 412.1552 found, 412.1535 required. |
| 1-42 | 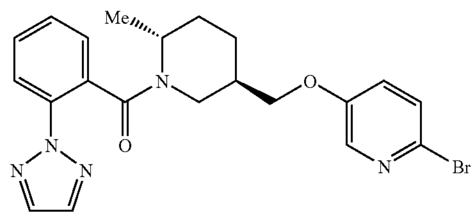 | 2-bromo-5-({(3R,6R)-6-methyl-1-[2-(2H-1,2,3-triazol-2-yl)benzoyl]piperidin-3-yl}methoxy)pyridine | 456.1039 found, 456.1030 required. |
| 1-43 | 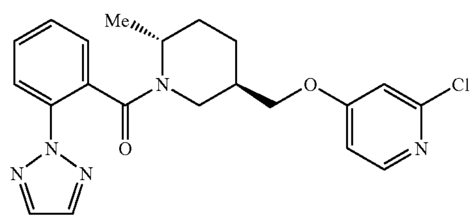 | 2-chloro-4-({(3R,6R)-6-methyl-1-[2-(2H-1,2,3-triazol-2-yl)benzoyl]piperidin-3-yl}methoxy)pyridine | 412.1553 found, 412.1535 required. |

40

TABLE 2

Table 2 shows representative data for the compounds of the Examples as orexin receptor OX1R and/or OX2R antagonists as determined by the foregoing assays.

| Cmpd | Structure | OX1R $K_i$ (nM) | OX2R $K_i$ (nM) |
|---|---|---|---|
| 2-1 | 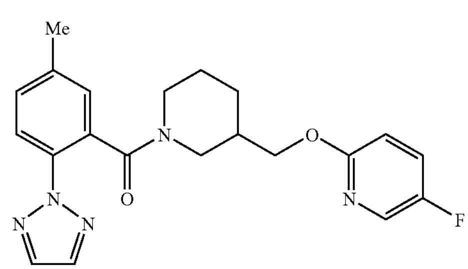 | 96 | 29 |

TABLE 2-continued

Table 2 shows representative data for the compounds of the Examples as orexin receptor OX1R and/or OX2R antagonists as determined by the foregoing assays.

| Cmpd | Structure | OX1R $K_i$ (nM) | OX2R $K_i$ (nM) |
|---|---|---|---|
| A-9 | 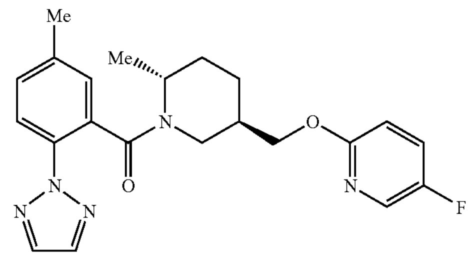 | 1.0 | 0.24 |
| B-3 | 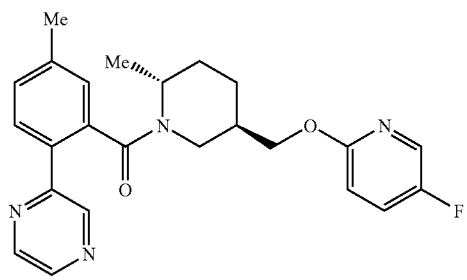 | 3.3 | 0.54 |
| C-4 | 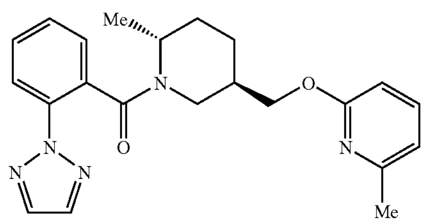 | 22 | 0.67 |
| E-5 | 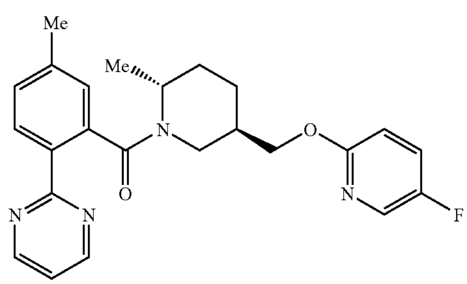 | 2.9 | 0.31 |
| F-4 | 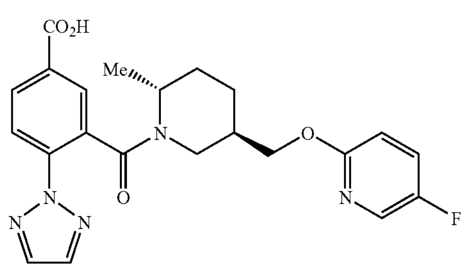 | 260 | 410 |
| G-1 | 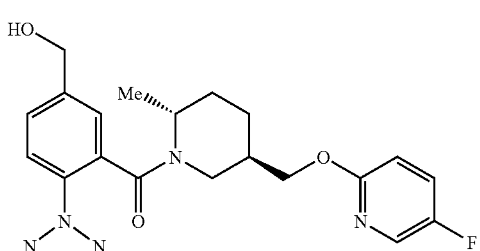 | 14 | 1.7 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound which is 2-{2-[((2R,5R)-5-{[(5-fluoropyridin-2-yl)oxy]methyl}-2-methylpiperidin-1-yl)carbonyl]-4-methylphenyl}pyrimidine or a pharmaceutically acceptable salt thereof.

2. A compound which is 2-{2-[((2R,5R)-5-{[(5-fluoropyridin-2-yl)oxy]methyl}-2-methylpiperidin-1-yl)carbonyl]-4-methylphenyl}pyrimidine.

3. A compound which is 2-{2-[((2R,5R)-5-{[(5-fluoropyridin-2-yl)oxy]methyl}-2-methylpiperidin-1-yl)carbonyl]-4-methylphenyl}pyrimidine in the form of a pharmaceutically acceptable salt thereof.

4. A pharmaceutical composition comprising a pharmaceutically acceptable carrier and a compound which is 2-{2-[((2R,5R)-5-{[(5-fluoropyridin-2-yl)oxy]methyl}-2-methylpiperidin-1-yl)carbonyl]-4-methylphenyl}pyrimidine or a pharmaceutically acceptable salt thereof.

5. A pharmaceutical composition comprising a pharmaceutically acceptable carrier and the compound 2-{2-[((2R,5R)-5-{[(5-fluoropyridin-2-yl)oxy]methyl}-2-methylpiperidin-1-yl)carbonyl]-4-methylphenyl}pyrimidine.

6. A pharmaceutical composition comprising a pharmaceutically acceptable carrier and the compound 2-{2-[((2R,5R)-5-{[(5-fluoropyridin-2-yl)oxy]methyl}-2-methylpiperidin-1-yl)carbonyl]-4-methylphenyl}pyrimidine in the form of a pharmaceutically acceptable salt thereof.

7. A method for treating insomnia in a human patient in need thereof which comprises administering to the patient a therapeutically effective amount of a compound which is 2-{2-[((2R,5R)-5-{[(5-fluoropyridin-2-yl)oxy]methyl}-2-methylpiperidin-1-yl)carbonyl]-4-methylphenyl}pyrimidine or a pharmaceutically acceptable salt thereof.

8. A method for treating insomnia in a human patient in need thereof which comprises administering to the patient a therapeutically effective amount of the compound 2-{2-[((2R,5R)-5-{[(5-fluoropyridin-2-yl)oxy]methyl}-2-methylpiperidin-1-yl)carbonyl]-4-methylphenyl}pyrimidine.

9. A method for treating insomnia in a human patient in need thereof which comprises administering to the patient a therapeutically effective amount of the compound 2-{2-[((2R,5R)-5-{[(5-fluoropyridin-2-yl)oxy]methyl}-2-methylpiperidin-1-yl)carbonyl]-4-methylphenyl}pyrimidine in the form of a pharmaceutically acceptable salt thereof.

* * * * *